(12) United States Patent
Romero

(10) Patent No.: US 7,804,297 B2
(45) Date of Patent: Sep. 28, 2010

(54) METHODOLOGY FOR INTERPRETATION AND ANALYSIS OF NMR DISTRIBUTIONS

(75) Inventor: Pedro Antonio Romero, Buenos Aires (AR)

(73) Assignee: Baker Hughes Incorporated, Houston, TX (US)

( * ) Notice: Subject to any disclaimer, the term of this patent is extended or adjusted under 35 U.S.C. 154(b) by 21 days.

(21) Appl. No.: 12/022,755

(22) Filed: Jan. 30, 2008

(65) Prior Publication Data

US 2009/0189604 A1 Jul. 30, 2009

(51) Int. Cl.
G01V 3/00 (2006.01)

(52) U.S. Cl. ...................................... 324/303
(58) Field of Classification Search .......... 324/300–322
See application file for complete search history.

(56) References Cited

U.S. PATENT DOCUMENTS

| | | | | |
|---|---|---|---|---|
| 5,698,979 | A | 12/1997 | Taicher et al. | 324/303 |
| 6,255,819 | B1 * | 7/2001 | Day et al. | 324/303 |
| 6,331,775 | B1 * | 12/2001 | Thern et al. | 324/303 |
| 6,337,568 | B1 * | 1/2002 | Tutunji et al. | 324/303 |
| 6,348,792 | B1 | 2/2002 | Beard et al. | 324/303 |
| 6,392,409 | B1 * | 5/2002 | Chen | 324/303 |
| 6,429,654 | B1 | 8/2002 | Itskovich et al. | 324/314 |
| 6,466,013 | B1 | 10/2002 | Hawkes et al. | 324/303 |
| 6,512,371 | B2 | 1/2003 | Prammer | 324/303 |
| 6,597,171 | B2 | 7/2003 | Hurlimann et al. | 324/303 |
| 6,600,315 | B1 * | 7/2003 | Heaton et al. | 324/303 |
| 6,642,715 | B2 * | 11/2003 | Speier et al. | 324/303 |
| 6,781,371 | B2 * | 8/2004 | Taherian et al. | 324/303 |
| 6,808,028 | B2 * | 10/2004 | Woodburn et al. | 175/48 |
| 6,954,066 | B2 * | 10/2005 | Siess et al. | 324/303 |
| 6,956,371 | B2 * | 10/2005 | Prammer | 324/303 |
| 6,972,564 | B2 | 12/2005 | Chen et al. | 324/303 |
| 7,049,815 | B2 | 5/2006 | Itskovich et al. | 324/303 |
| 7,196,516 | B2 * | 3/2007 | Blanz et al. | 324/303 |
| 7,309,983 | B2 * | 12/2007 | Freedman | 324/303 |
| 7,502,691 | B2 * | 3/2009 | Romero | 702/7 |
| 7,511,487 | B2 * | 3/2009 | Badry et al. | 324/303 |

OTHER PUBLICATIONS

P. Romero, *Method for Characterization of Rock Quality Based on Winland-Pittman and Timur-Cotes Equations Applied to NMR Lalboratory Data*, SPWLA 45th Annual Logging Symposium, Jun. 6-9, 2004, pp. 1-13, 12 Figs. Meeting, pp. 360-363.

\* cited by examiner

Primary Examiner—Brij B Shrivastav
Assistant Examiner—Dixomara Vargas
(74) Attorney, Agent, or Firm—Mossman Kumar & Tyler PC

(57) ABSTRACT

Pulse sequences are applied to a fluid in an earth formation in a static magnetic field and NMR spin echo signals are obtained. The signals are inverted to give $T_2$ distributions at a plurality of depths. Similarities between logs of the $T_2$ bins with resistivity and/or gamma ray logs are used to identify and subtract contributions to the NMR signal from oil. having internal gradients. From the received signals, relaxation and diffusion characteristics of the fluid are determined. The determination takes into account the internal field gradients. It is emphasized that this abstract is provided to comply with the rules requiring an abstract which will allow a searcher or other reader to quickly ascertain the subject matter of the technical disclosure. It is submitted with the understanding that it will not be used to interpret or limit the scope or meaning of the claims. 37 CFR 1.72(b).

20 Claims, 18 Drawing Sheets
(5 of 18 Drawing Sheet(s) Filed in Color)

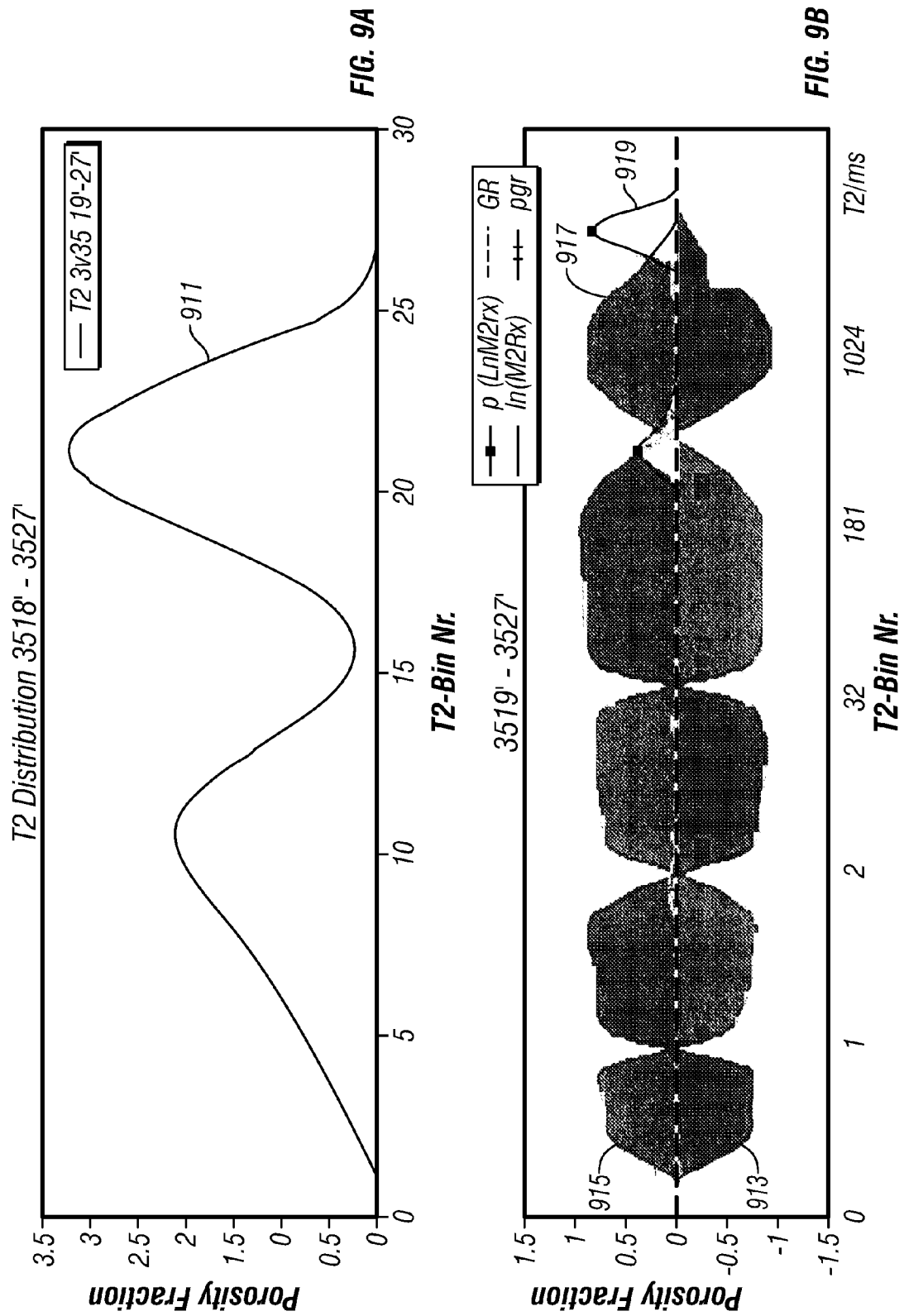

| | CBW | BVI | BVM | OIL | GAS | HEAV... |
|---|---|---|---|---|---|---|
| HI | 1 | 1 | 1 | 1 | 1 | 1 |
| T2(1) | 6.1 | 9.0 | 19.0 | 18.0 | 24.0 | 18.0 |
| T2(2) | 9.0 | 17.0 | 25.0 | 23.0 | 25.0 | 23.0 |
| D(1) | 14.8 | 14.8 | 14.8 | 13.8 | 16.8 | 13.8 |
| D(2) | 16.8 | 16.8 | 16.8 | 14.8 | 17.8 | 14.8 |
| PPOR | 0.5 | 0.7 | 7.5 | 2.8 | 2.3 | 2.8 |

| SETTING | APPLY | OK | CANCEL |
|---|---|---|---|

METHODOLOGY FOR INTERPRETATION AND ANALYSIS OF NMR DISTRIBUTIONS

FIELD OF THE DISCLOSURE

This disclosure relates to apparatus and techniques for making nuclear magnetic resonance (NMR) measurements in boreholes and to methods for determining magnetic characteristics of formations traversed by a borehole. Specifically, the disclosure relates to design an accurate NMR measurement technique, which is aimed at defining the diffusion properties of the fluid in the pore matrix in the presence of the internal magnetic field gradients.

BACKGROUND OF THE DISCLOSURE

A variety of techniques have been used in determining the presence and in estimating quantities of hydrocarbons (oil and gas) in earth formations. These methods are designed to determine parameters of interest, including among other things, porosity, fluid content, and permeability of the rock formation surrounding the borehole drilled for recovering hydrocarbons. Typically, the tools designed to provide the desired information are used to log the borehole. Much of the logging is done after the boreholes have been drilled. More recently, boreholes have been logged while drilling of the boreholes. This is referred to as measurement-while-drilling ("MWD") or logging-while-drilling ("LWD"). Measurements have also been made when tripping a drillstring out of a borehole: this is called measurement-while-tripping ("MWT").

One evolving technique uses nuclear magnetic resonance (NMR) logging tools and methods for determining, among other things porosity, hydrocarbon saturation and permeability of the rock formations. NMR logging tools excite the nuclei of the fluids in the geological formations in the vicinity of the borehole so that certain parameters such as spin density, longitudinal relaxation time (generally referred to in the art as "$T_1$"), and transverse relaxation time (generally referred to as "$T_2$") of the geological formations can be estimated. From such measurements, formation parameters such as porosity, permeability and hydrocarbon saturation are determined, which provides valuable information about the make-up of the geological formations and the amount of extractable hydrocarbons.

A typical NMR tool generates a static magnetic field $B_0$ in the vicinity of the borehole and an oscillating field $B_1$ in a direction perpendicular to $B_0$. This oscillating field is usually applied in the form of short-duration pulses. The purpose of the $B_0$ field is to polarize the magnetic moments of nuclei parallel to the static field and the purpose of the $B_1$ field is to rotate the magnetic moments by an angle controlled by the width $t_p$ and the amplitude $B_1$ of the oscillating pulse. For NMR logging, the most common sequence is the Carr-Purcell-Meiboom-Gill ("CPMG") sequence that can be expressed as $$TW-90-(\tau-180-\tau-echo)_n \quad (1)$$

where TW is a wait time, 90 is a 90° tipping pulse, 180 and is a 180° refocusing pulse and $2\tau=TE$ is the interecho spacing.

After being tipped by 90°, the magnetic moment precesses around the static field at a particular frequency known as the Larmor frequency $\omega$, given by $\omega=\gamma B_0$, where $B_0$ is the field strength of the static magnetic field and $\gamma$ is the gyromagnetic ratio. At the same time, the magnetic moments return to the equilibrium direction (i.e., aligned with the static field) according to a decay time known as the "spin-lattice relaxation time" or $T_1$. Inhomogeneities of the $B_0$ field result in dephasing of the magnetic moments and to remedy this, a 180° pulse is included in the sequence to refocus the magnetic moments. This refocusing gives a sequence of n echo signals. These echo sequences are then processed to provide information about the relaxation times. U.S. Pat. No. 6,466,013 to Hawkes et al. and U.S. Pat. No. 6,429,654 to Itskovich et al., both having the same assignee as the present disclosure, teach the use of modified CPMG pulse sequences with reduced power requirements in which the refocusing pulse angle may be less than 180°. These modified pulse sequences may be referred to as optimal rephrasing pulse sequences (ORPS).

Also associated with the spin of molecular nuclei is a second relaxation time, $T_2$, called the transverse or spin—spin relaxation time. At the end of a 90° tipping pulse, all the spins are pointed in a common direction perpendicular, or transverse, to the static field, and they all precess at the Larmor frequency. However, because of small fluctuations in the static field induced by other spins or paramagnetic impurities, the spins precess at slightly different frequencies and the transverse magnetization dephases with a relaxation time $T_2$.

Interpretation of NMR core or log data is often started by inverting the time-domain CPMG (or ORPS) echo decay into a $T_2$ parameter domain distribution. In general, the $T_2$ of fluids in porous rocks depends on the pore-size distribution and the type and number of fluids saturating the pore system. Because of the heterogeneous nature of porous media, $T_2$ decays exhibit a multiexponential behavior. The basic equation describing the transverse relaxation of magnetization in fluid saturated porous media is $$M(t) = \int_{T_{2\min}}^{T_{2\max}} P(T_2) e^{-t/T_2} \, dT_2 \quad (2)$$

where M is magnetization and effects of diffusion in the presence of a magnetic field gradient have not been taken into consideration. Eq. (2) is based on the assumption that diffusion effects may be ignored. In a gradient magnetic field, diffusion causes atoms to move from their original positions to new ones which also causes these atoms to acquire different phase shifts compared to atoms that did not move. This contributes to a faster rate of relaxation.

The effect of field gradients is given by an equation of the form $$\frac{1}{T_2} = \frac{1}{T_{2bulk}} + \frac{1}{T_{2surface}} + \frac{1}{T_{2diffusion}} \quad (3)$$

where the first two terms on the right hand side are related to bulk relaxation and surface relaxation while the third term is related to the field gradient G by an equation of the form $$T_{2diffusion} = \frac{C}{TE^2 \cdot G^2 \cdot D} \quad (4)$$

where TE is the interecho spacing, C is a constant and D is the diffusivity of the fluid.

U.S. Pat. No. 6,512,371 to Prammer et al. discloses a well logging system and method for detecting the presence and estimating the quantity of gaseous and liquid hydrocarbons in the near-borehole zone. The system uses a gradient-based, multiple-frequency NMR logging tool to extract signal components characteristic for each type of hydrocarbon. Measurements at different frequencies are interleaved to obtain, in a single logging pass, multiple data streams corresponding to different recovery times and/or diffusivity for the same spot in the formation.

One of the main difficulties in defining self-diffusion parameters of the fluid in the pore matrix is related to the fact that different fluids having the same relaxation times and different diffusion coefficients cannot be effectively separated. Due to the practical limitation of the signal-to-noise ratio, none of the existing inversion techniques allow an effective and stable reconstruction of both the relaxation and diffusion spectra.

Another difficulty in relaxation and diffusion spectra reconstruction is caused by internal magnetic gradients. Typically, the values of the internal gradients are unknown. Thus, the diffusion parameters cannot be correctly defined if the internal gradients are not considered in both the measurement and interpretation scheme. These have been addressed, for example, in U.S. Pat. No. 6,597,171 to Hurlimann et al., and in U.S. Pat. No. 5,698,979 to Taicher et al. having the same assignee as the present application and the contents of which are incorporated herein by reference, and U.S. Pat. No. 7,049,815 to Itskovich et al., having the same assignee as the present application and the contents of which are incorporated herein by reference. A common aspect of all the prior art methods discussed above is that they do not consider measurements by other logs in the processing of the NMR data, and measurements at one depth are processed substantially independently of measurements and other depths.

SUMMARY OF THE DISCLOSURE

One embodiment of the disclosure is method of evaluating an earth formation. The method includes conveying a logging tool into a borehole, obtaining nuclear magnetic resonance (NMR) signals at a plurality of depths in the borehole, and processing the NMR signals to obtained a distribution of a relaxation time at each of the plurality of depths, each of the distributions comprising a plurality of bins, producing from the plurality of relaxation time distributions a plurality of NMR bin logs of relaxation time values corresponding to each of the plurality of bins, determining a measure of similarity of a first log indicative of hydrocarbon content in the formation with each of the plurality of NMR bin logs, and using the measure of similarity for each of the plurality of NMR bin logs to identify a subset of the plurality of NMR bin logs indicative of hydrocarbon. The NMR signals may be spin-echo signals and the relaxation time may be a transverse relaxation time $T_2$. The measure of similarity may be a Pearson correlation coefficient and/or a p-value characterizing a probability of an observed correlation coefficient. The first log may be a gamma ray log and/or a resistivity log. Determining the measure of similarity may include a cross-correlation of the first log with at least one of the plurality of NMR bin logs and/or a determination of the mutual entropy between the first log and at least one of the plurality of NMR bin logs. The method may include obtaining additional spin echo signals at each of the plurality of depths while applying an external magnetic field gradient, processing the spin echo signals and the additional spin echo signals to obtain a distribution of a diffusion coefficient (D) at each of the plurality of depths, each of the distribution of diffusion coefficients comprising a plurality of diffusion bins, producing from the plurality of diffusion coefficient distributions a plurality of diffusion coefficient bin logs of diffusion coefficient bin values corresponding to each of the plurality of diffusion bins, determining a measure of similarity of the first log with each of the plurality of diffusion coefficient bin logs, and using the measure of similarity for each of the plurality of diffusion coefficient bin logs to identify a subset of the logs indicative of hydrocarbon. The method may further include using the identified subset of the logs and a $T_2$ distribution at least one of the plurality of depths to obtain a modified $T_2$ distribution responsive primarily to water in the formation. The method may further include estimating from the modified distribution a water saturation, a clay-bound water, bound water irreducible, movable water and/or a permeability. The method may further include conveying the logging tool into the borehole on a conveyance device selected from a wireline and a drilling tubular.

Another embodiment of the disclosure is an apparatus for evaluating an earth formation. The apparatus includes a logging tool configured to be conveyed into a borehole, the logging tool further configured to obtain nuclear magnetic resonance (NMR) signals at a plurality of depths in the borehole. The apparatus also includes at least one processor configured to processed the NMR signals to obtain a distribution of a relaxation time at each of the plurality of depths, each of the distributions comprising a plurality of bins; and use the plurality of relaxation time distributions to produce a plurality of NMR bin logs of relaxation time values corresponding to each of the plurality of bins; determine a measure of similarity of a first log indicative of hydrocarbon content in the formation with each of the plurality of NMR bin logs; and use the measure of similarities for each of the plurality of NMR bin logs to identify a subset of the NMR bin logs indicative of hydrocarbon. The NMR signals may be spin-echo signals and the relaxation time may be a transverse relaxation time $T_2$. The processor may be configured to use a measure of similarity that is a Pearson correlation coefficient and/or a p-value characterizing a probability of an observed correlation coefficient. The apparatus may further include a resistivity logging tool and/or a gamma-ray logging tool and the processor may be configured to use as the first log a gamma ray log and/or a resistivity log. The processor may be configured to determine the measure of similarity by using a cross-correlation of the first log with at least one of the plurality of NMR bin logs and/or a determination of the mutual entropy between the first log and at least one of the plurality of NMR bin logs. The logging tool may further configured to obtain additional spin echo signals at each of the plurality of depths while applying an external magnetic field gradient, and the processor may be further configured to process the spin echo signals and the additional spin echo signals to obtain a distribution of a diffusion coefficient at each of the plurality of depths, each of the distribution of diffusion coefficients comprising a plurality of diffusion bins; produce, from the plurality of diffusion coefficient distributions a plurality of diffusion coefficient bin logs of diffusion coefficient being values corresponding to each of the plurality of diffusion bins; determine a measure of similarity of the first log with each of the plurality of diffusion coefficient bin logs; and use the measure of similarity for each of the plurality of diffusion coefficient bin logs identify a subset of the logs indicative of hydrocarbon. The processor may be further configured to use the identified subset of logs and a $T_2$ distribution at least one of the plurality of depths to obtain a modified $T_2$ distribution responsive primarily to water in the formation. The processor may be further configured to estimate from the modified distribution of water saturation, clay-bound water, bound water irreducible, movable water and/or permeability. The apparatus may further include a conveyance device configured to convey the logging tool into the borehole, the conveyance device being a wireline or a drilling tubular.

Another embodiment of the disclosure is a computer-readable medium for use with an apparatus for evaluating an earth formation. The apparatus includes a logging tool configured to be conveyed into a borehole, the logging tool further configured to obtain spin-echo signals at a plurality of depths in the borehole. The medium includes instructions which enable at least one processor to process the spin echo signals to obtain a distribution of a transverse relaxation time ($T_2$) at each of the plurality of depths, each of the distributions comprising a plurality of vanes; use the plurality of relaxation time distributions to produce a plurality of NMR bin logs of relaxation time values corresponding to each of the plurality of bins; determine a measure of similarity of a first log indicative of hydrocarbon content in the formation with each of the plurality of NMR bin logs; and used to measure of similarity for each of the plurality of NMR bin logs to identify a subset of the NMR bin logs indicative of hydrocarbon. The computer readable medium may be a ROM, an EPROM, an EAROM, a flash memory, and/or an optical disk.

BRIEF DESCRIPTION OF THE DRAWINGS

The file of this patent contains at least one drawing executed in color: Copies of this patent with color drawing(s) will be provided by the Patent and Trademark Office upon request and payment of the necessary fee. The present disclosure is best understood with reference to the following figures in which like numerals refer to like elements, and in which:

FIG. 9(a) shows an exemplary $T_2$ distribution over a depth interval that includes oil and FIG. 9(b) shows different measures of similarity of the $T_2$ distribution with gamma ray and resistivity logs;

DETAILED DESCRIPTION OF THE DISCLOSURE

Figure 1:
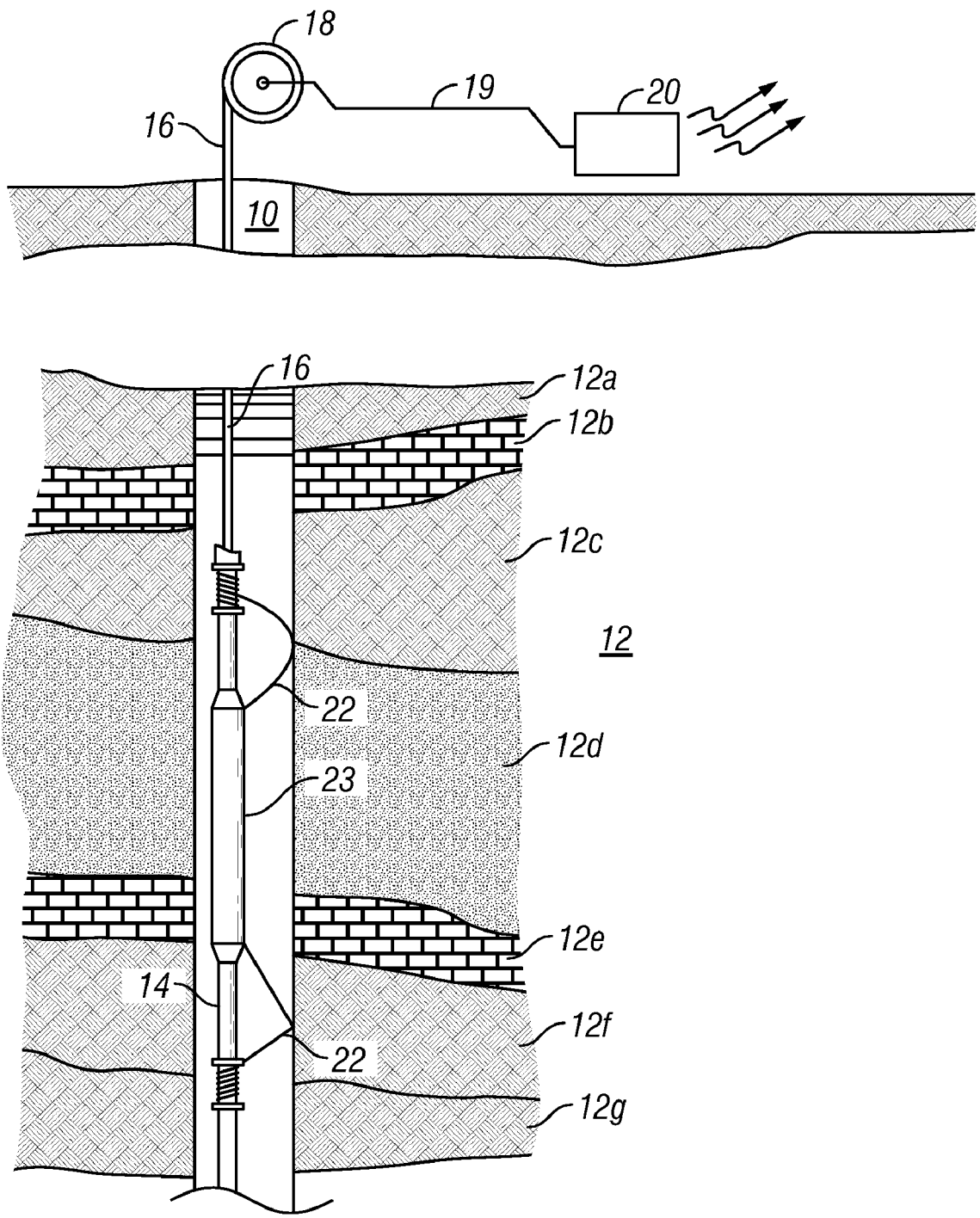
FIG. 1 depicts diagrammatically an NMR logging tool in a borehole.

FIG. 1 depicts a borehole 10 drilled in a typical fashion into a subsurface geological formation 12 to be investigated for potential hydrocarbon producing reservoirs. An NMR logging tool 14 has been lowered into the hole 10 by means of a cable 16 and appropriate surface equipment (represented diagrammatically by a reel 18) and is being raised through the formation 12 comprising a plurality of layers 12a through 12g of differing composition, to log one or more of the formation's characteristics. The NMR logging tool may be provided with bowsprings 22 to maintain the tool in an eccentric position within the borehole with one side of the tool in proximity to the borehole wall. The permanent magnets 23 provide the static magnetic field. Signals generated by the tool 14 are passed to the surface through the cable 16 and from the cable 16 through another line 19 to appropriate surface equipment 20 for processing, recording, display and/or for transmission to another site for processing, recording and/or display. Alternatively, the processor may be located at a suitable position (not shown) downhole, e.g., in the logging tool 14.

Figure 2:
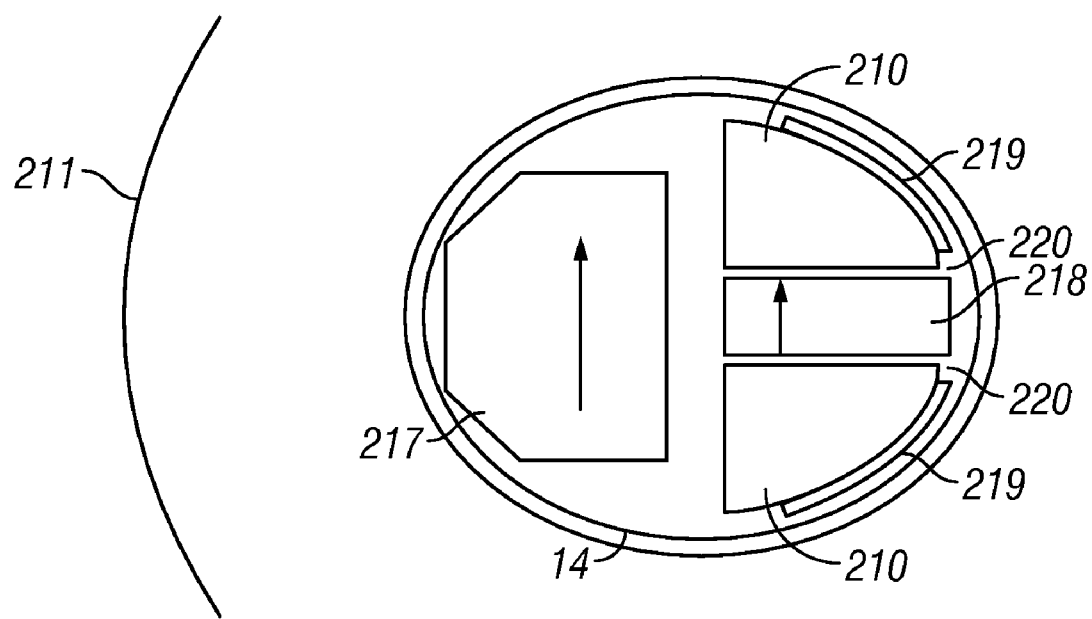
FIG. 2 (prior art) shows an exemplary configuration of magnets, antenna and shield suitable for use with the present disclosure.

FIG. 2 (prior art) schematically illustrates an exemplary embodiment of an apparatus suitable for use with the method of the present disclosure. This is discussed in detail in U.S. Pat. No. 6,348,792 of Beard et al., having the same assignee as the present disclosure and the contents of which are fully incorporated herein by reference. The tool cross-sectional view in FIG. 2 illustrates a main magnet 217, a second magnet 218 and a transceiver antenna comprising wires 219 and core material 210. The arrows depict the polarization (e.g., from the South pole to the North pole) of the main magnet 217 and the secondary magnet 218. A noteworthy feature of the arrangement shown in FIG. 2 is that the polarization of the magnets providing the static field is towards the side of the tool, rather than towards the front of the tool (the right side of FIG. 2).

The second magnet 218 is positioned to augment the shape of the static magnetic field by adding a second magnetic dipole in close proximity to the RF dipole defined by the wires 219 and the soft magnetic core 210. This positioning moves the center of the effective static dipole closer to the RF dipole, thereby increasing the azimuthal extent of the region of examination. The second magnet 218 also reduces the shunting effect of the high permeability magnetic core 210 on the main magnet 217. In the absence of the second magnet, the DC field would be effectively shorted by the core 210. Thus, the second magnet, besides acting as a shaping magnet for shaping the static field to the front of the tool (the side of the main magnet) also acts as a bucking magnet with respect to the static field in the core 210. Those versed in the art will recognize that the bucking function and a limited shaping could be accomplished simply by having a gap in the core; however, since some kind of field shaping is required on the front side of the tool, in one embodiment of the disclosure, the second magnet serves both for field shaping and for bucking. If the static field in the core 210 is close to zero, then the magnetostrictive ringing from the core is substantially eliminated.

Within the region of investigation, the static field gradient is substantially uniform and the static field strength lies within predetermined limits to give a substantially uniform Larmor frequency. Those versed in the art will recognize that the combination of field shaping and bucking could be accomplished by other magnet configurations than those shown in FIG. 2.

NMR spin echo signals are obtained using the apparatus of FIG. 2. Optionally, additional measurements may be made using an external gradient field as discussed in Reiderman. Measurements made with the gradient field enable the determination of diffusivity. The manner in which these measurements are used is discussed next.

Figure 3:
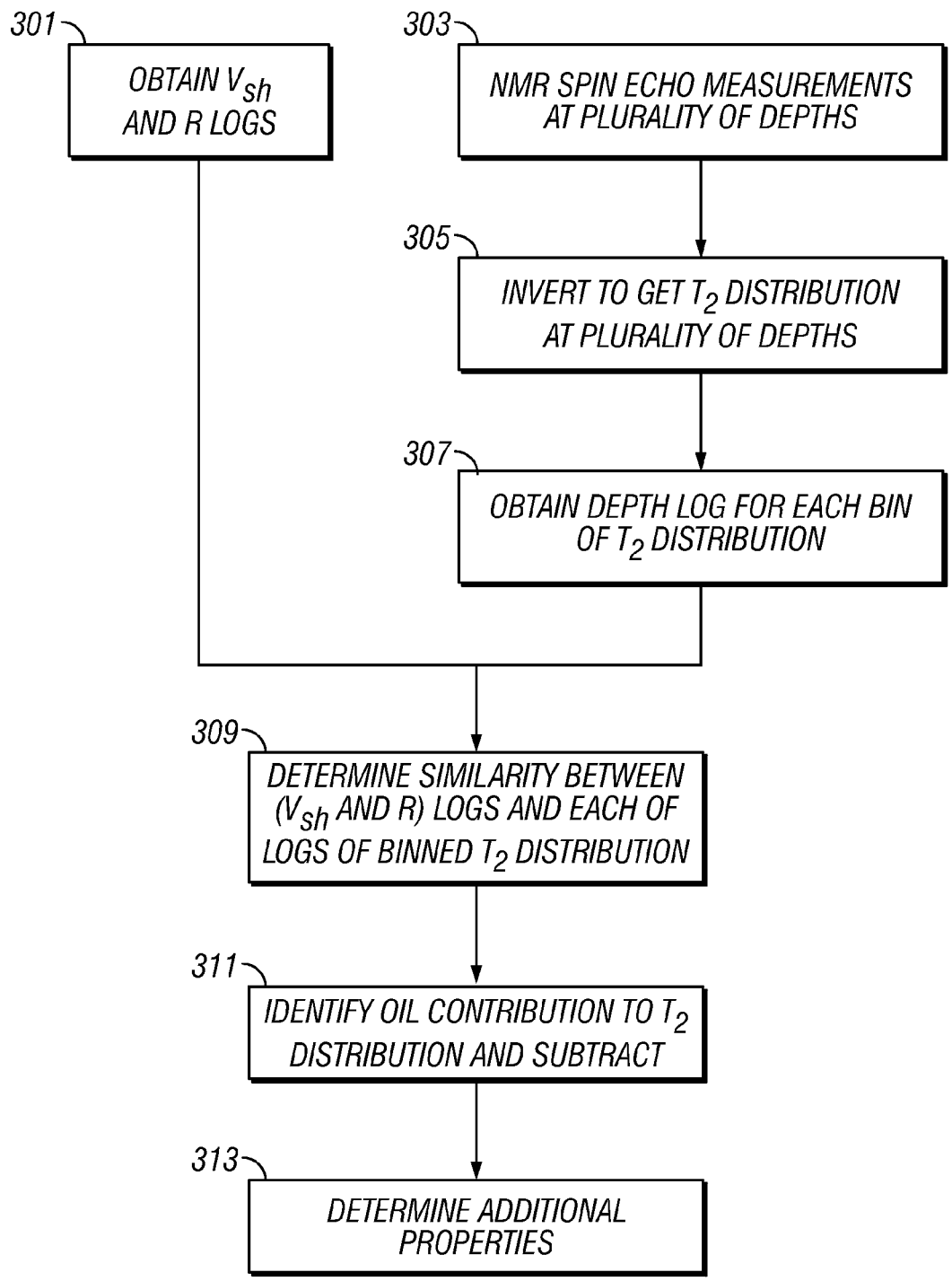
FIG. 3 shows a flow chart illustrating some of the important features of the present disclosure.

Shown in FIG. 3 is a flow chart outlining some of the steps of the present disclosure. NMR measurements are obtained 303. In addition, gamma ray logs indicative of the shale content of the formation, and resistivity logs are obtained 301. The measurements of resistivity and gamma ray logs may be done simultaneously with the acquisition of the NMR data or, as is more common, the resistivity and/or gamma ray logs may be obtained in a different logging run than the NMR logs.

Figure 5:
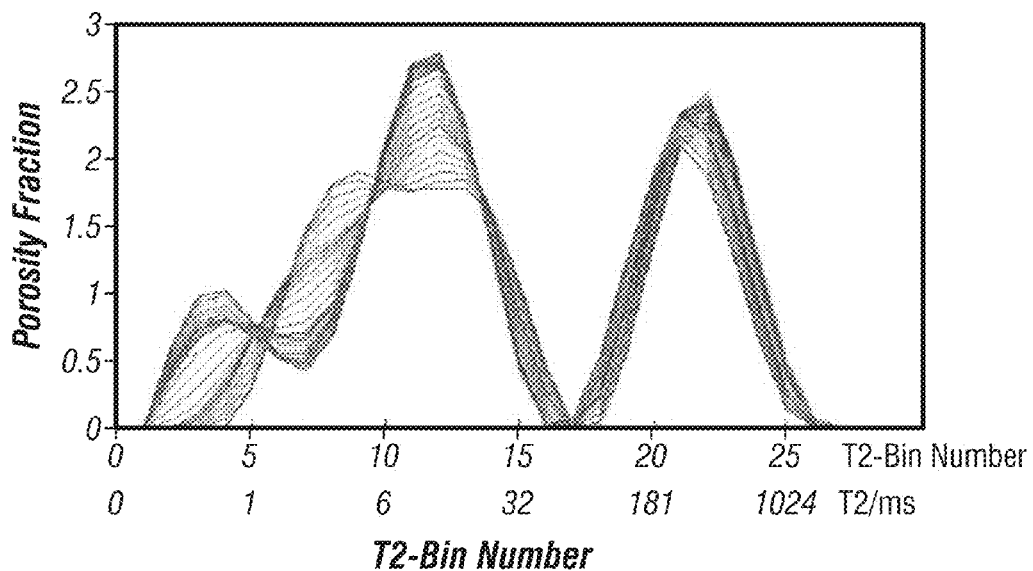
FIG. 5 shows an exemplary plot of $T_2$ distributions obtained by processing of the data in FIG. 4 at a plurality of depths.

The NMR measurements are inverted using prior art methods to obtain a $T_2$ distribution at each of a plurality of depths 305. The $T_2$ distribution is characterized by its values in a plurality of bins. FIG. 5 shows an exemplary plot of the $T_2$ distribution at a plurality of depths. In the example shown, approximately 30 bins were used with a total time of greater than 1024 ms.

Figure 4:
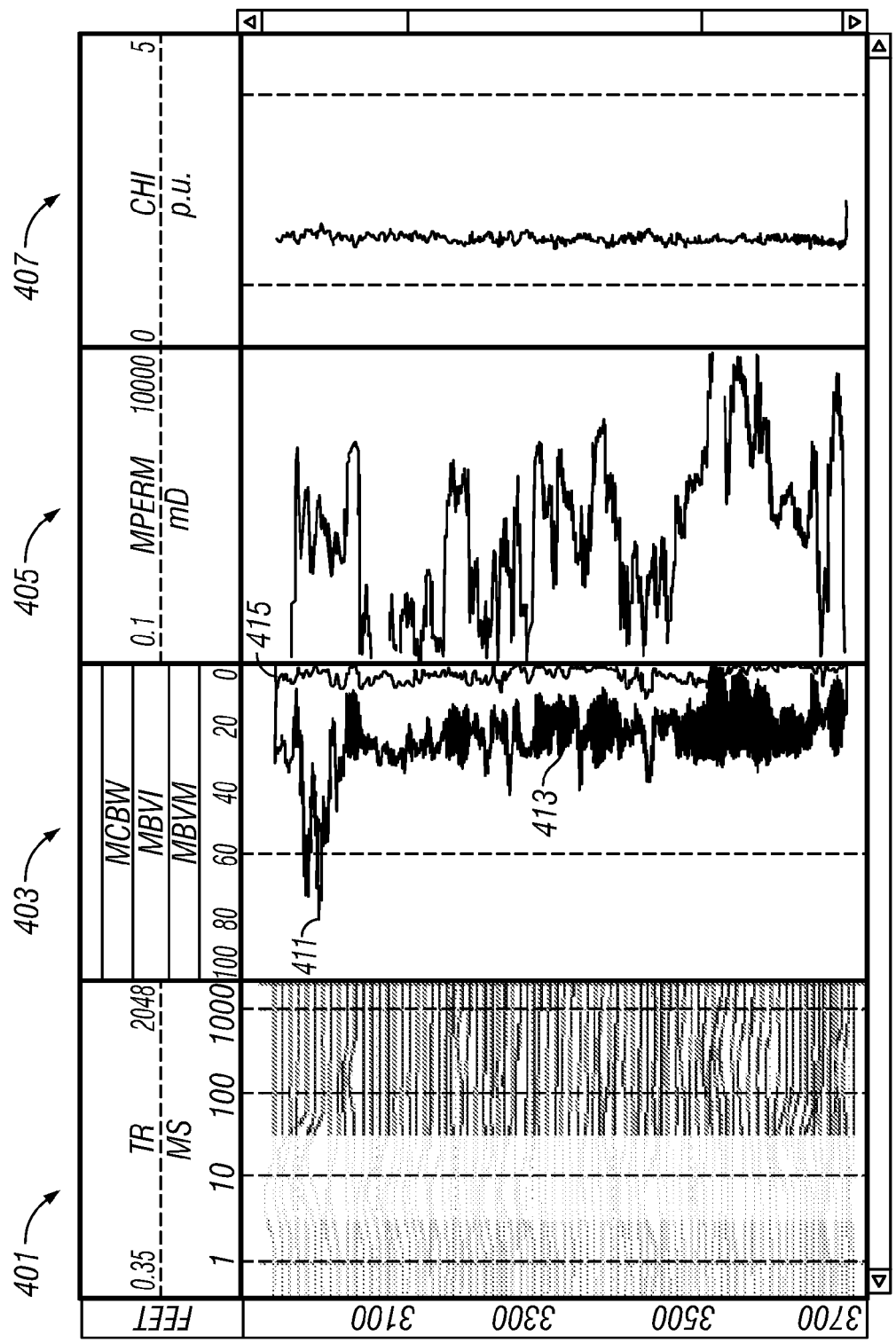
FIG. 4 (prior art) shows an exemplary display of results obtained using a prior art method for processing of NMR data.

Digressing briefly, FIG. 4 shows an exemplary display of prior art processing. Track 1 401 shows the $T_2$ distribution from a well over a depth range of around 600 ft. Track 2 403 shows the bound volume irreducible 411, the bound water moveable 415 and the clay bound water 417. Track 3 405 shows the determined permeability and track 4 407 shows the misfit in the determination of permeability and porosities. The total porosity includes clay-bound water (CBW), capillary bound water (also known as Bulk Volume Irreducible or BVI), movable water and hydrocarbons. See U.S. Pat. No. 6,972,564 to Chen.

Figure 6:
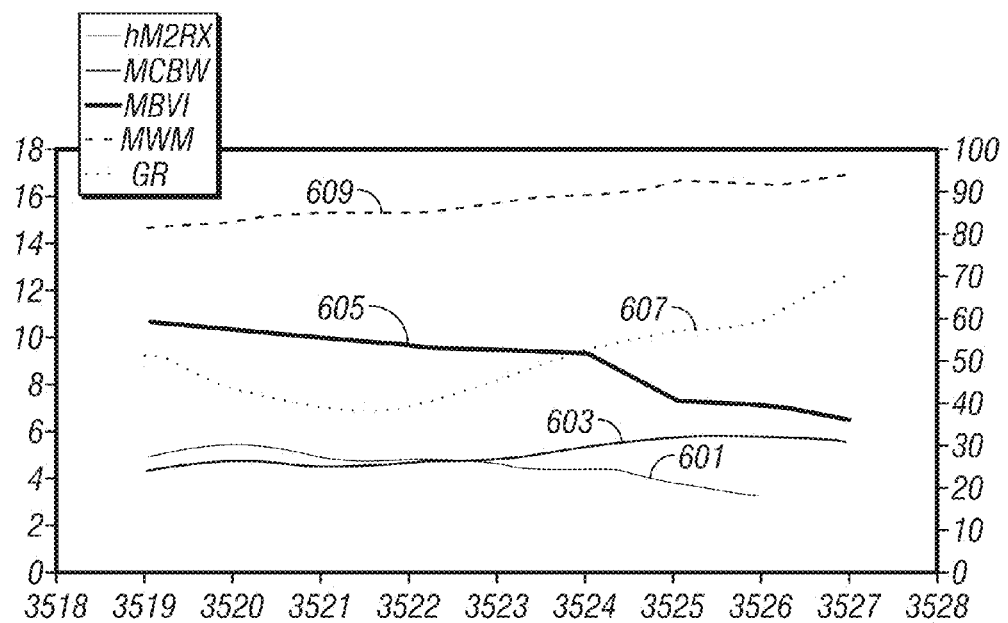
FIG. 6 shows plots of resistivity, gamma ray, clay bound water, bound volume irreducible and movable water over a portion of the depth interval shown in FIGS. 4 and 5.
Figure 7:
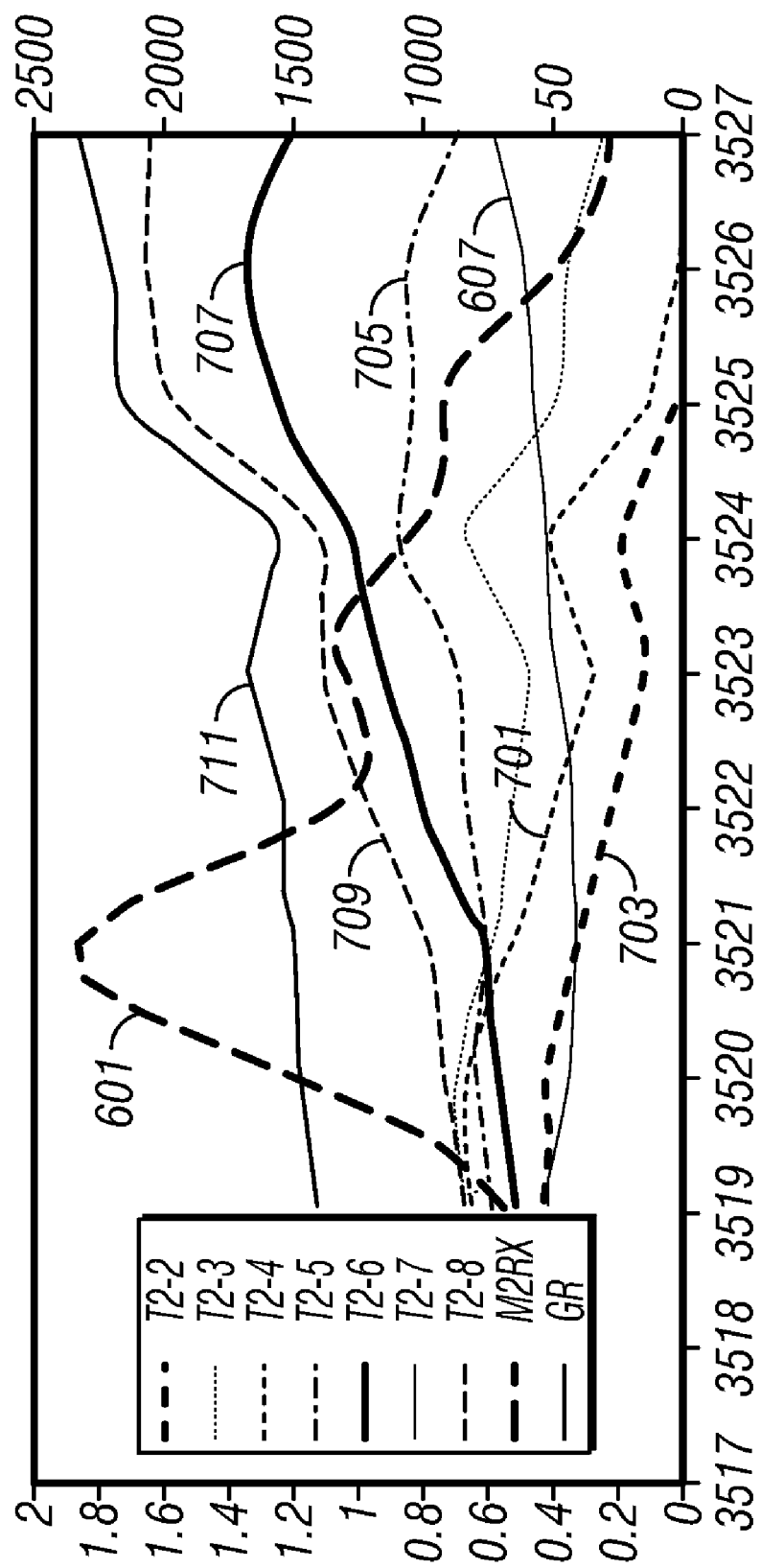
FIG. 7 shows plots of resistivity, gamma ray and selected $T_2$ bin logs over the depth interval of FIG. 6.

An important feature of the present disclosure is that the NMR data are sorted to produce an NMR bin log for each of the bins of the distribution 307. The method of the present disclosure is based upon identifying and using similarities between the NMR bin logs and the resistivity and gamma ray logs. FIG. 6 shows a display of the resistivity 601 log over an 8 ft. (2.44 m) interval, the gamma ray log 607, a log of clay-bound water (from FIG. 4), a plot of BVI 605 and a plot of bound water movable 609. FIG. 7 shows the gamma ray and resistivity plots, and in addition, shows a log of NMR bins 2-8 over the same depth interval 701, 703, 705, 707, 709, and 711.

The present method is based on two principles. First, an increase in the resistivity log is commonly due to an increase in the oil in the formation (provided the gamma ray indicates a small amount of shale). Accordingly, in depths in which the resistivity is high, the bin that characterizes oil in the formation will tend to have a larger value. Thus, referring back to FIG. 3, a depth log is obtained for each bin of the $T_2$ distribution 307. Still referring to FIG. 3, a measure of similarity is determined between the $T_2$ bin logs and the resistivity log and the gamma ray log 309. The measure of similarity is discussed below.

The similarity test can be performed using any linear or non-linear correlation, depending on the case. However, tests results suggest using cross correlation or only the correlation matrix if there is no depth shift between the logs. Once the oil peak has been found, the correlation to the viscosity can be established using known models. Furthermore, by removing the effects of the oil exemplified by the oil peak 311 from the original $T_2$ distribution, the water $T_2$ distribution can be obtained and hence the water saturation, $S_w$. This is discussed further below after the discussion of FIG. 14. In the special case of heavy oil, and probably in more general cases, but depending on the oil viscosity and degree of water saturation, the $T_2$ bin logs with negative correlation with the resistivity logs and their gradients are more likely to represent the movable water, to be drained by the oil when the oil saturation increases. By this way it is possible to trace back the $T_2$ distribution of the water saturation using a Gaussian curve fitting or an approach like that in U.S. patent application Ser. No. 11/445,023 of Georgi et al. which also generates a scale for correlating the $T_2$ bin with the grain size. When a model for the water $T_2$ distribution is obtained, a model for the capillary pressure curve and rock quality (P. Romero, SPWLA 2004) and for the relative permeability (Corey-Burdine) can be established 313. Furthermore, a cross plot of the hydrocarbon $T_2$ distribution vs. $T_2$ distribution for the 100% water saturation can be built, which indicates the zones of different productivity indexes. This is discussed below with reference to FIGS. 16-19.

Figure 8A:
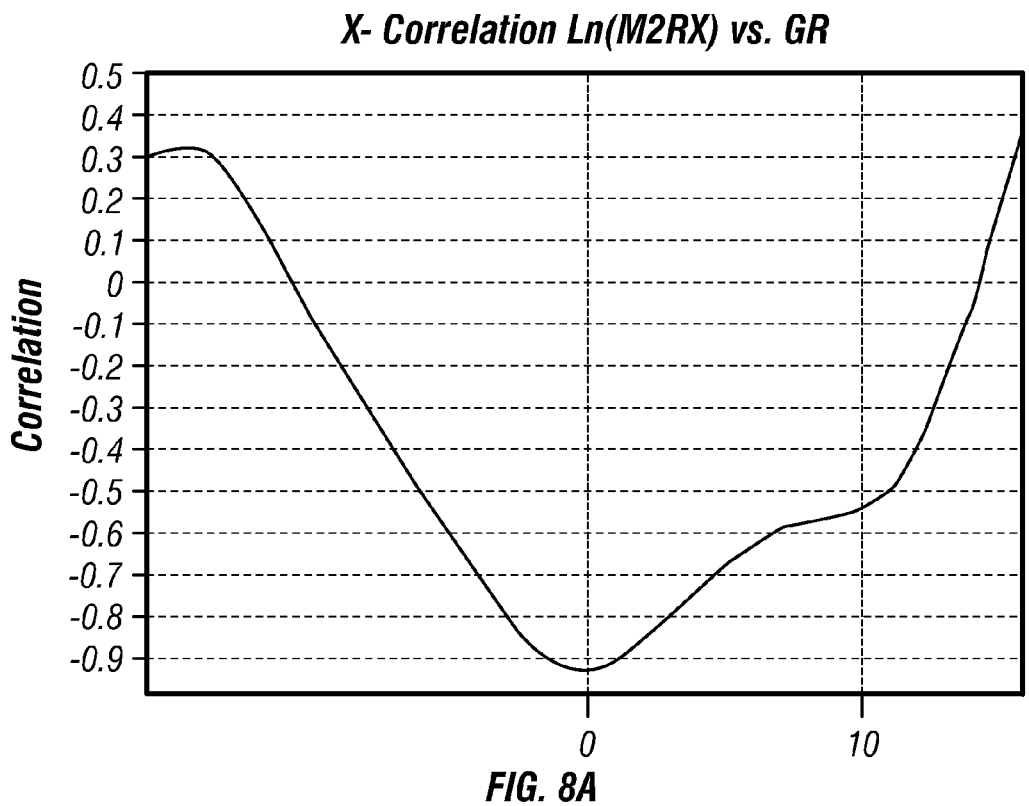
FIG. 8(a)-(d) illustrate exemplary cross-correlations between loges measured in different runs.
Figure 8B:
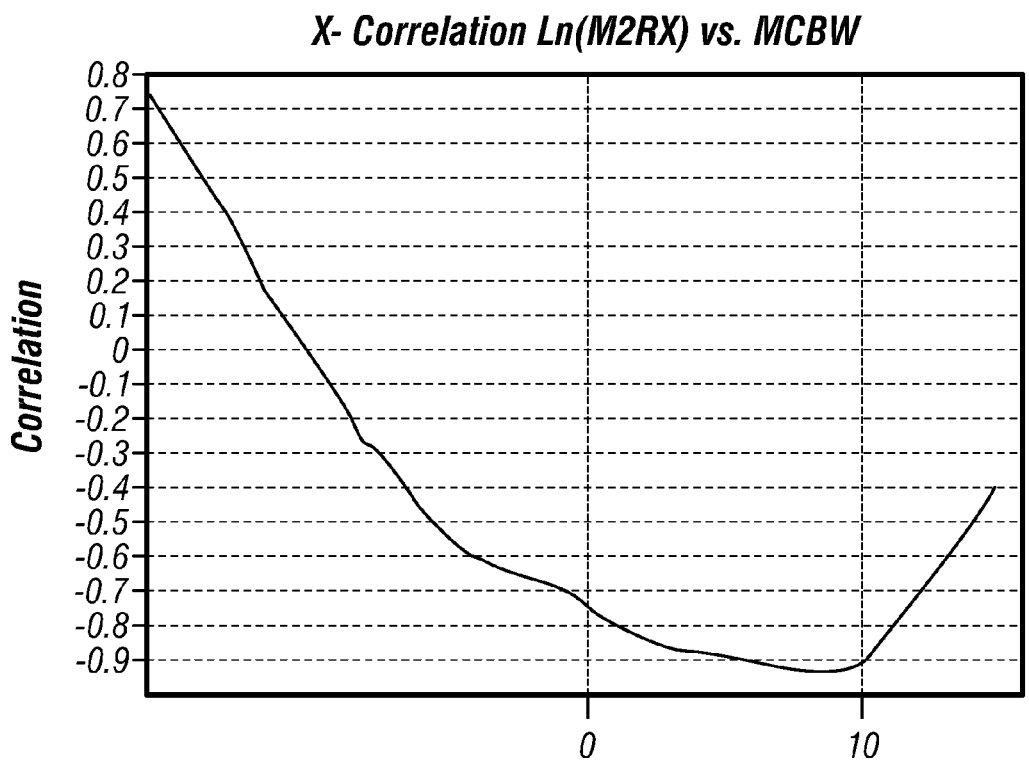
Figure 8C:
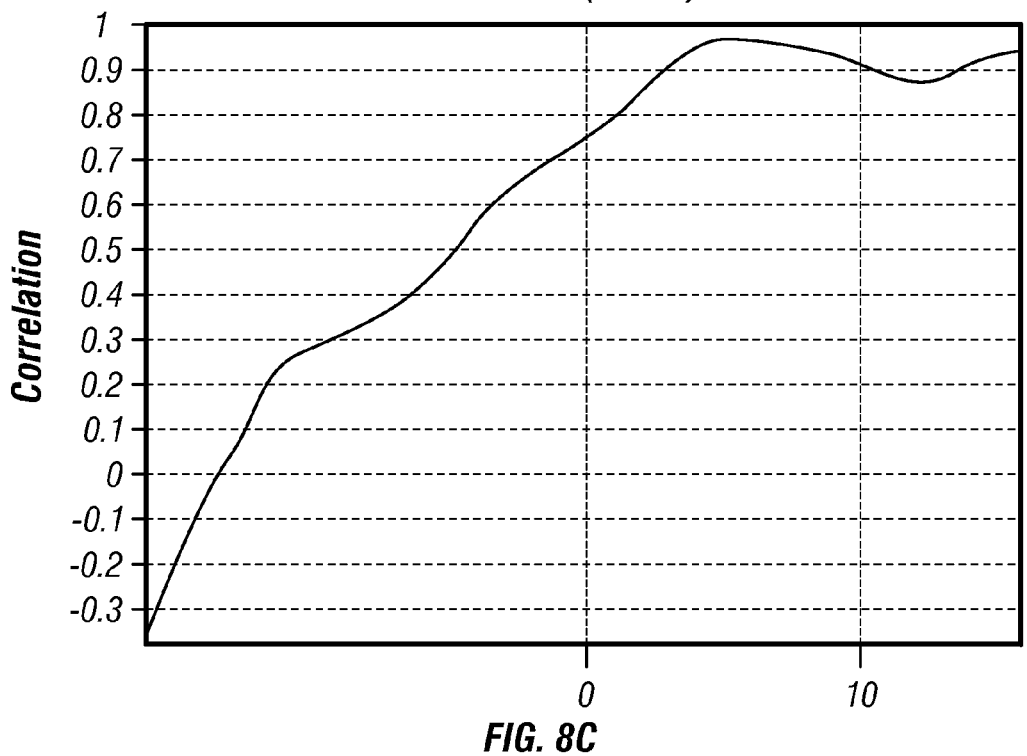
Figure 8D:
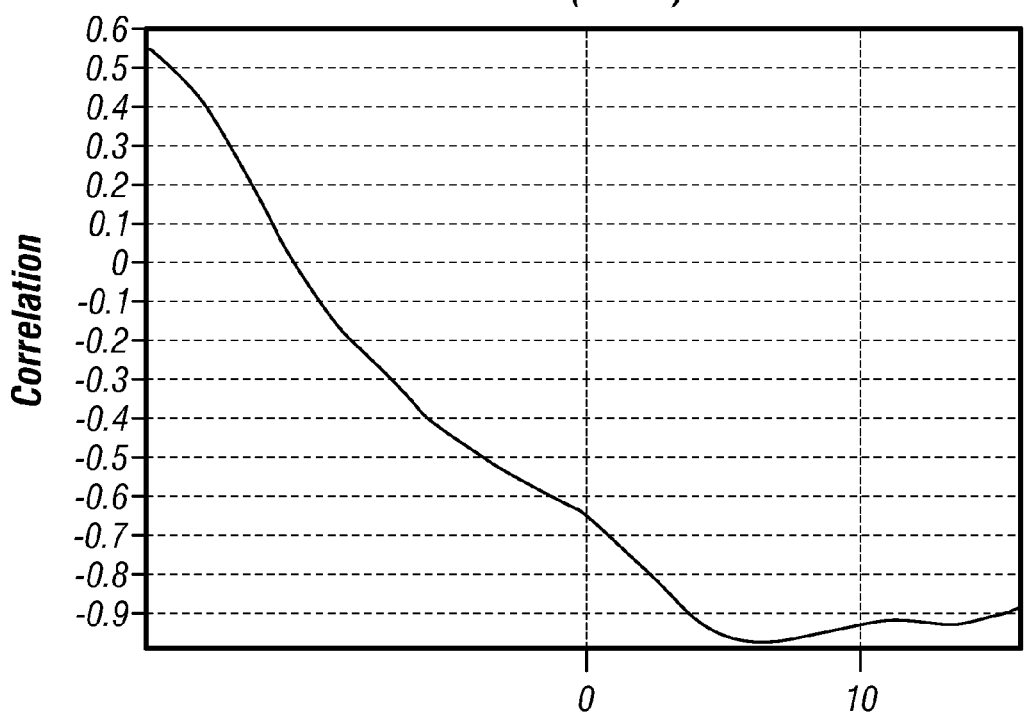

Those versed in the art would recognize that logs made at different times in the same borehole may not be perfectly registered. This is illustrated in FIG. 8. Shown in FIG. 8(a) is the cross-correlation between the resistivity and the gamma ray logs. As expected, there is a negative correlation between the two and a time shift of zero because the logs were measured in the same logging run. FIG. 8(b) shows the cross-correlation between the resistivity and Clay bound water log. Since the latter is derived from NMR measurements made in a separate logging run, there is a depth shift of approximately 10 ft. (2.44 m) between the logs. A similar shift is noted in FIG. 8(c) of the bound volume irreducible and in FIG. 8(d) for the movable water. Such a cross-correlation step, while not illustrated in FIG. 3, may be necessary before determination of similarity 309. As an alternative to using a peak of the cross-correlation technique for different time shifts, the mutual entropy between two shifted traces may be used. The entropy is defined as $H(x) = -E\{x \log(P(x))\}$ where $H(.)$ is the entropy, $E\{.\}$ is the expected value and $P(.)$ is the probability density function.

We next discuss measures of similarity that are used in the present disclosure between the different logs. These are for exemplary purposes only and other measures of similarity could be used with the present method.

The first concept is that of covariance. This is a measure of how much the variations of the variables are interrelated. Consider a random vector $$X = (X_1, X_2, \ldots X_n) \tag{5.}$$

For any pair of components, the covariance is defined by the expectation $$\mathrm{cov}(X_i, X_k) = \Sigma_{ik} = E\{(X_i - \mu_i)(X_k - \mu_k)\} \tag{6},$$

Where $\mu_i$ and $\mu_k$ are the mean values of $X_i$ and $X_k$. The covariance is then given by the covariance matrix:

$$\vec{\Sigma} = \begin{bmatrix} \Sigma_{1,1} & \Sigma_{1,2} & \Sigma_{1,3} & \cdots & \Sigma_{1,n} \\ \Sigma_{2,1} & \Sigma_{2,2} & \Sigma_{2,3} & \cdots & \Sigma_{1,n} \\ \Sigma_{3,1} & \Sigma_{3,2} & \Sigma_{3,3} & \cdots & \Sigma_{3,n} \\ \vdots & \vdots & \vdots & \ddots & \vdots \\ \Sigma_{n,1} & \Sigma_{n,2} & \Sigma_{n,3} & \cdots & \Sigma_{n,n} \end{bmatrix}. \quad (7)$$

The second concept is that of correlation. Correlation is a dimension less than measure of linear dependence of random variables. Pearson's Correlation Coefficient r is the best estimate of correlation of normally distributed variables:

$$\rho_{ik} = \frac{\text{cov}(x_i, x_k)}{\sigma_i \sigma_k}, \quad (8)$$

where $\sigma_i$ and $\sigma_k$ are the standard deviations of $X_i$ and $X_k$. The correlation matrix is:

$$\vec{\rho} = \begin{bmatrix} \rho_{1,1} & \rho_{1,2} & \rho_{1,3} & \cdots & \rho_{1,n} \\ \rho_{2,1} & \rho_{2,2} & \rho_{2,3} & \cdots & \rho_{1,n} \\ \rho_{3,1} & \rho_{3,2} & \rho_{3,3} & \cdots & \rho_{3,n} \\ \vdots & \vdots & \vdots & \ddots & \vdots \\ \rho_{n,1} & \rho_{n,2} & \rho_{n,3} & \cdots & \rho_{n,n} \end{bmatrix}. \quad (9)$$

Corresponding to the correlation matrix is a correlation/p-value matrix:

$$\vec{\rho} = \begin{bmatrix} & \rho_{1,2} & \rho_{1,3} & \cdots & \rho_{1,n} \\ \rho_{2,1} & & \rho_{2,3} & \cdots & \rho_{1,n} \\ \rho_{3,1} & \rho_{3,2} & \rho_{3,3} & \cdots & \rho_{3,n} \\ \vdots & \vdots & \vdots & \ddots & \vdots \\ \rho_{n,1} & \rho_{n,2} & \rho_{n,3} & \cdots & \end{bmatrix}. \quad (10)$$

In simple terms, a p-value is the probability of obtaining a finding as a result of chance alone.

Turning now to FIG. 9, shown in FIG. 9(a) is an exemplary averaged $T_2$ distribution 911 derived over a depth interval from measurements made in a well. The plot shows the averaged $T_2$ as a function of bin number. 913 is the Pearson correlation coefficient between the NMR bin logs and the gamma ray log, while 915 is the Pearson correlation coefficient between the NMR bin logs and the resistivity log. Denoted by 919 is the p-value of resistivity, while 917 is the p-value of the gamma ray. It should be emphasized that the values for 913, 915, 917 and 919 for any particular bin are obtained using the NMR $T_2$ bin log for that particular bin. It can be seen that except for the largest bin numbers, the p-values are close to zero, meaning that there is a very low probability that the observed correlations are a result of chance.

Figure 10A:
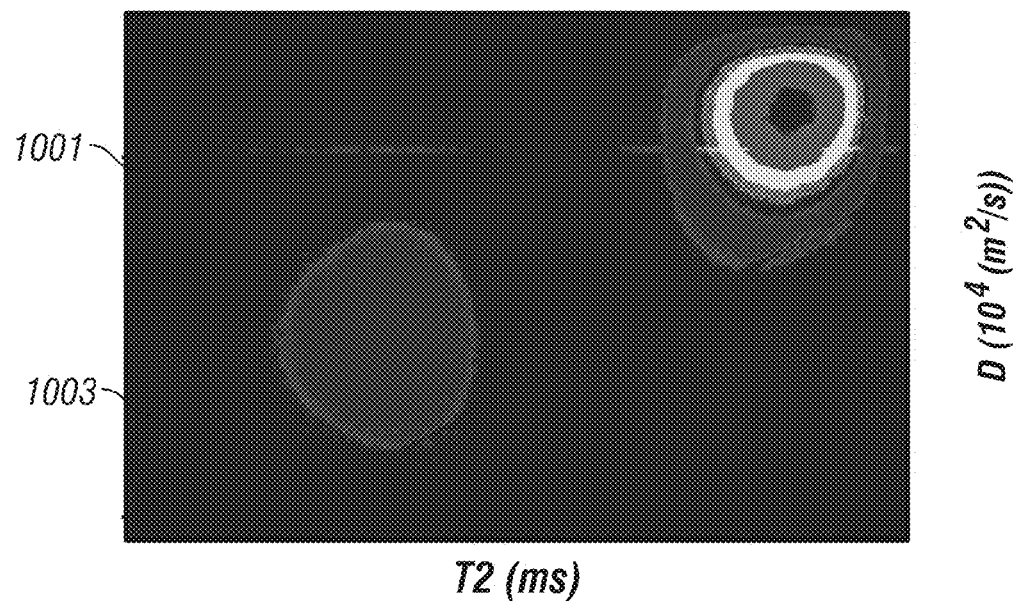
FIG. 10 (in color) shows (a) a 2-D distribution of the data in the $T_2$—diffusivity plane, (b) the distribution in 1-D with respect to the $T_2$—axis, (c) the distribution in 1-D with respect to the diffusivity axis, and (d) a portion of a graphic display interface.
Figure 10B:
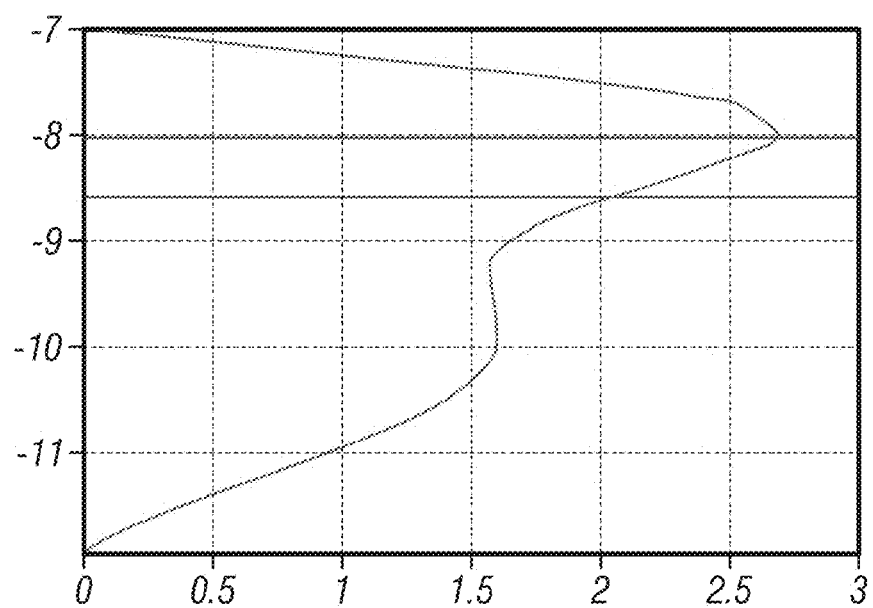
Figures 10C, 10D:
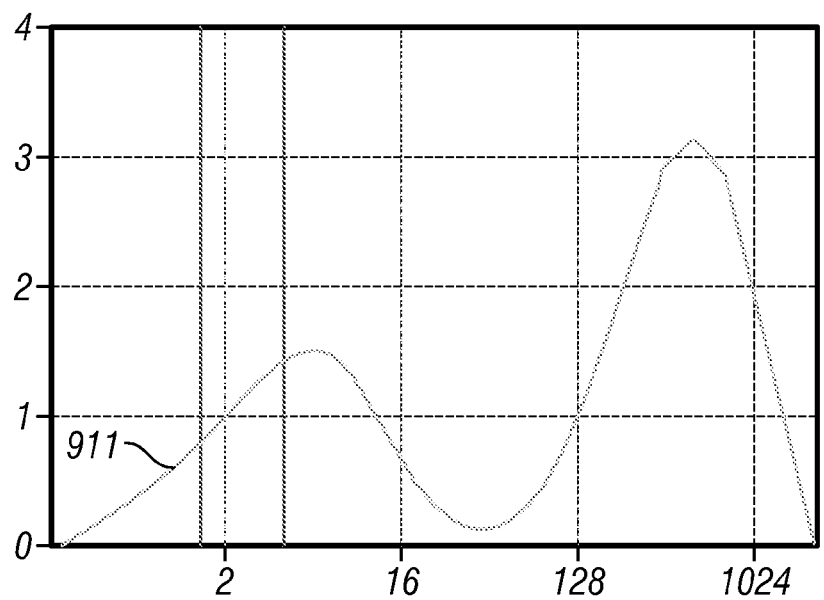

A similar processing may be carried out with measurements made with a field gradient to give plots as a function of diffusivity. FIG. 10(c) shows the same $T_2$ distribution 911 from FIG. 9(a). FIG. 10(a) is a 2-D plot in the $T_2$-diffusivity plane and FIG. 10(b) is a plot of the Pearson correlation coefficient as a function of $T_2$ distribution and diffusivity. The line 1001 shows the expected position for a water-wet rock while 1003 shows the expected trend for oil-saturated rock. The depth interval corresponding to this plot was a water saturated interval. A point to note is that examples given later using 1-D $T_2$ distributions can also be done with 1-D Diffusivity distributions and 2-D distributions in the $T_2$-diffusivity plane.

Figure 11:
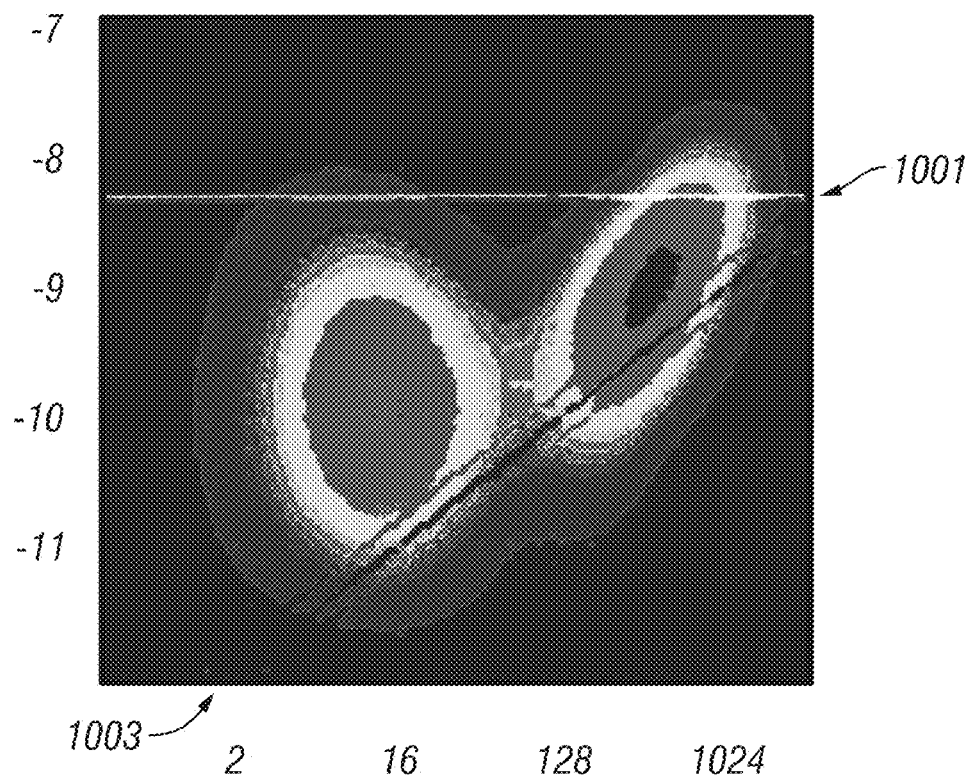
FIG. 11 (in color) shows a 2-D distribution of data in the $T_2$-diffusivity plane for a depth interval that includes oil.
Figure 12A:
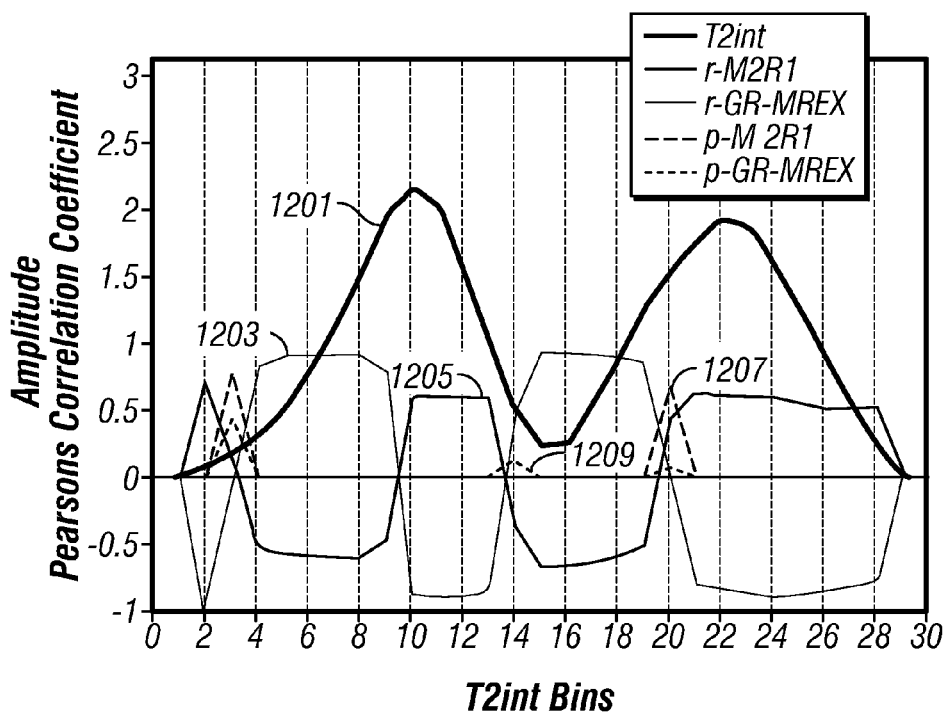
FIG. 12(a)-(b) show the Pearson correlation coefficient and the p-value for data in FIG. 11.
Figure 12B:
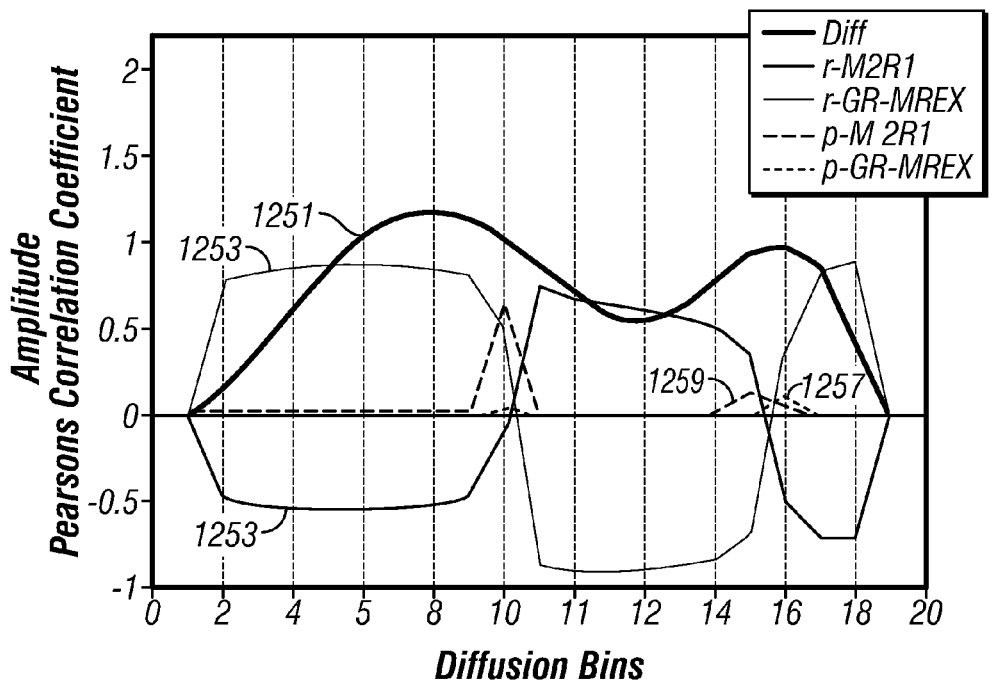

FIG. 11 shows a Pearson correlation 2-D plot of another example of field data in which there is considerable amount of oil present as indicated by the high values near the oil line 1003. 1201 in FIG. 12(a) shows the averaged NMR $T_2$ distribution for this interval, 1203 shows the Pearson correlation coefficient between the gamma ray log and the averaged $T_2$ bin log, 1205 shows the Pearson correlation coefficient between the resistivity log the $T_2$ bin log. 1207 and 1209 show the p-values corresponding to 1203 and 1205 respectively. Shown in FIG. 12(b) is the averaged diffusivity 1251, the Pearson correlations of the diffusivity bin logs with gamma ray (1253) and resistivity (1255) and the corresponding p-values 1257, 1259.

Figure 13:
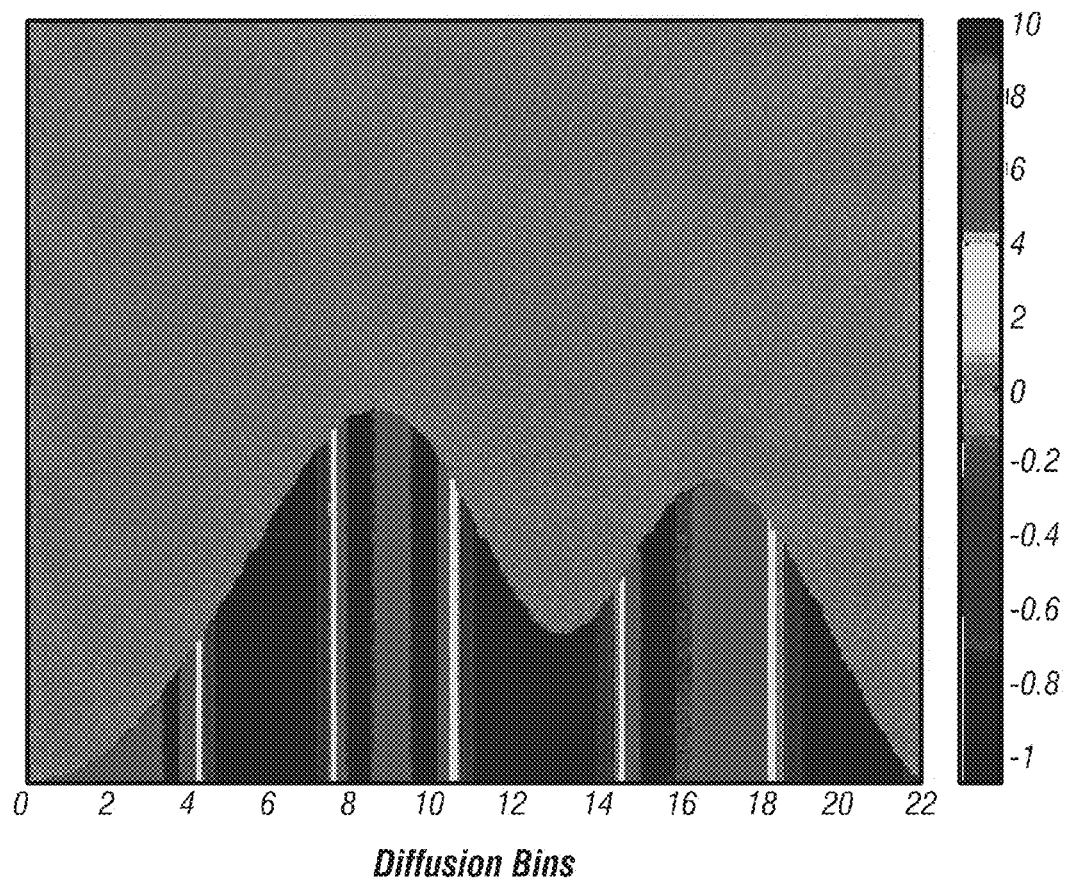
FIG. 13 (in color) shows the $T_2$ distribution for the data of FIG. 11 color coded according to a measure of similarity.

FIG. 13 shows the averaged $T_2$ distribution that has been color coded to show the correlation of the $T_2$ bin log for a particular bin with the resistivity log. The large correlations in bins 8-10 are indicative of a significant amount of oil in the interval.

Figure 14:
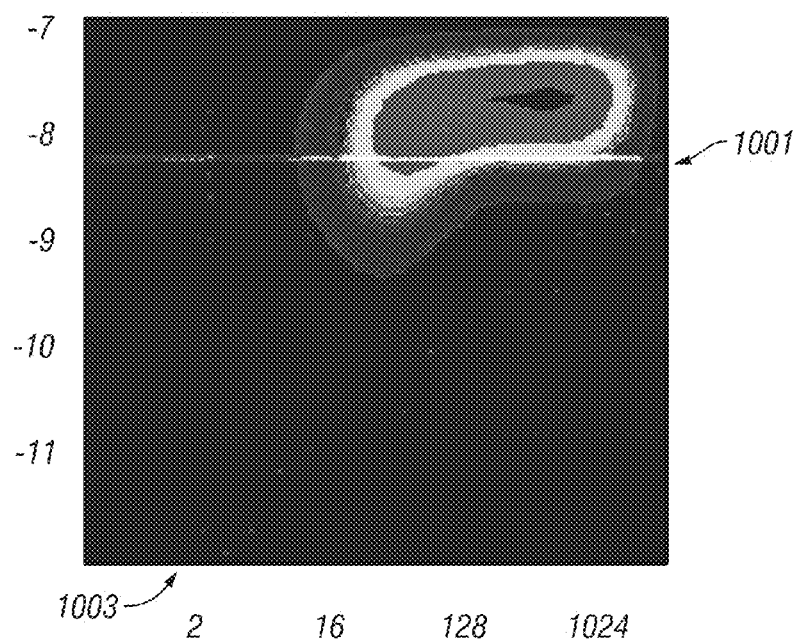
FIG. 14 (in color) shows a 2-D distribution of data in the $T_2$-diffusivity plane for a depth interval that is water-bearing.
Figure 15A:
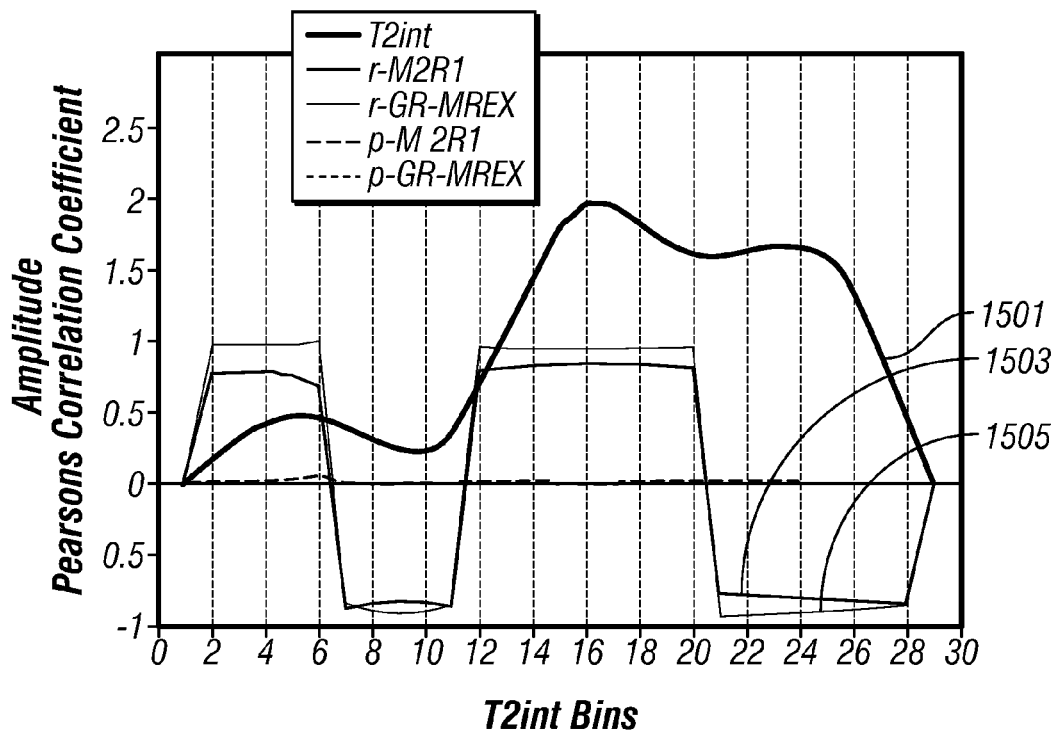
FIG. 15(a)-(b) show the Pearson correlation coefficient and the p-value for data in FIG. 14.
Figure 15B:
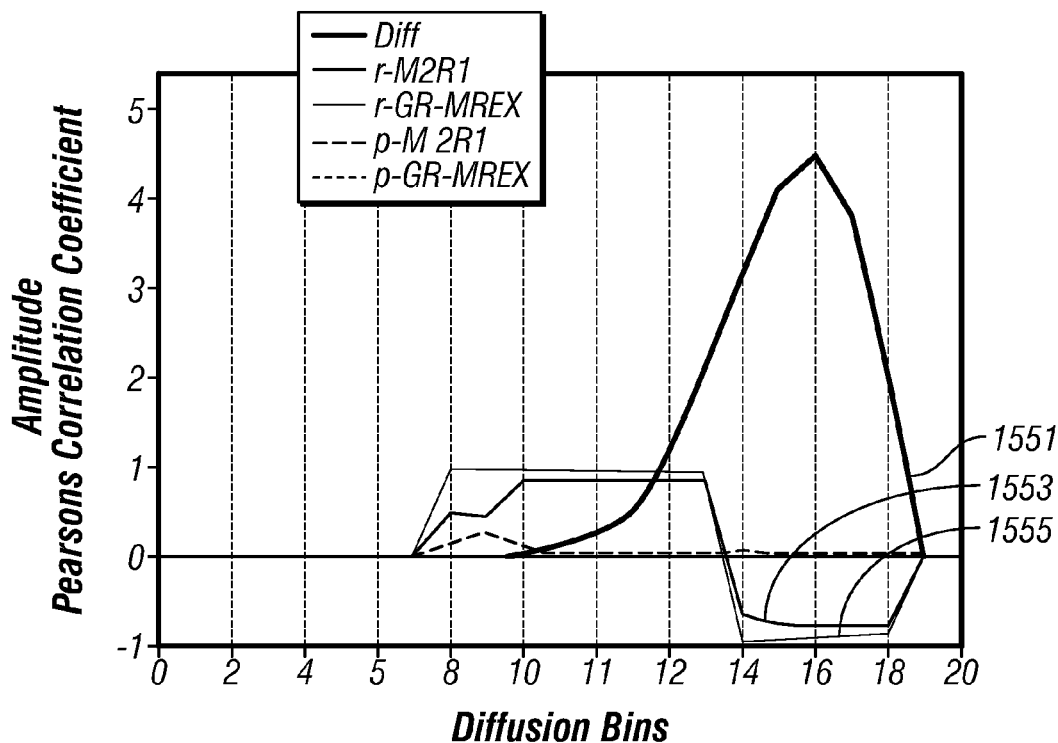

FIG. 14 shows the Pearson correlation as a function of $T_2$ and diffusivity for a water wet interval. Note the high values near the water line 1001. 1501 in FIG. 15(a) shows the averaged NMR $T_2$ distribution for this interval, 1403 shows the Pearson correlation coefficient between the gamma ray log and the averaged $T_2$ bin log, 1505 shows the Pearson correlation coefficient between the resistivity log the $T_2$ bin log. The p-values are not plotted as they are close to zero. Shown in FIG. 15(b) is the averaged diffusivity 1551, the Pearson correlations of the diffusivity bin logs with gamma ray (1553) and resistivity (1555).

Returning now to FIG. 11, in one embodiment of the invention, a 2-D filtering is applied to the data to attenuate portions of the data near the oil line 1003. After this filtering is done, projecting the filtered data onto the $T_2$ axis will give an estimate of the $T_2$ distribution of water in the formation. Alternatively, filtering may be done to attenuate data that is not near the oil line 1003, projecting the filtered data onto the $T_2$ axis, and subtracting the projected distribution from the original $T_2$ distribution to give an estimate of the water $T_2$ distribution.

Figure 16:
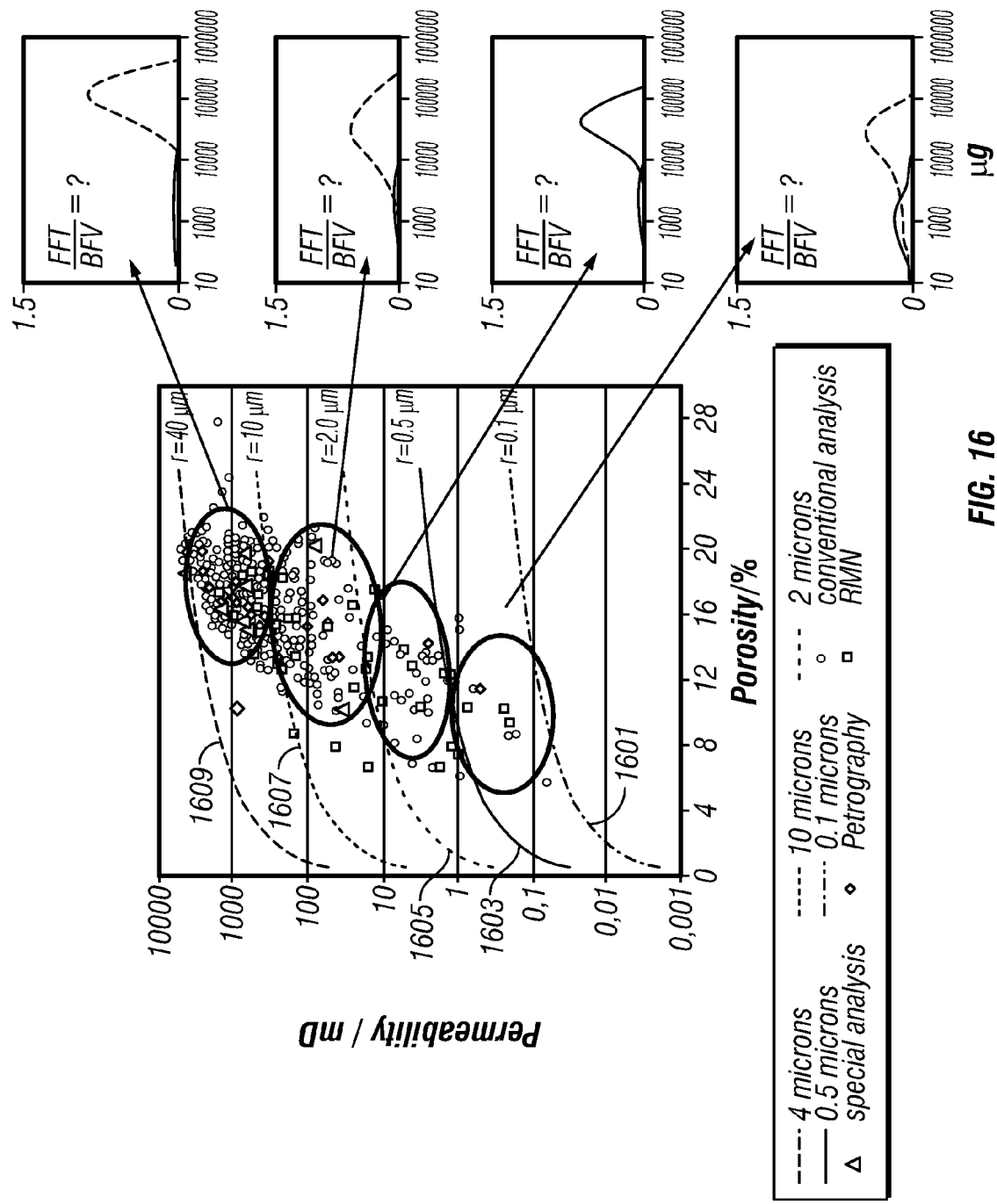
FIG. 16 shows petrofacies and the corresponding $T_2$ distribution at 100% and irreducible water saturation.

FIG. 16 shows a plot of a number of rock samples of the permeability in mD (ordinate) against the porosity (ordinate). Also indicated on the plot are curves of constant pore throat sizes: for 0.1 µm (1601), 0.5 µm (1603), 2.0 µm (1605), 10 µm (1607) and 40 µm (1609). Also shown in the side-panel of FIG. 16 are plots of the $T_2$ distribution for the four groups of rocks of different grain sizes. In each of the plots in the side-panel, the dominant curve is for 100% water saturation while the light colored curve is for irreducible water saturation. The curves on the plot are the limits of the facies (families or clusters) found in the sample set. These facies are characterized by the pore throat size and have a characteristic $T_1$ or $T_2$ distributions. In case that the real $T_1$ or $T_2$ distributions are not known, one can take a characteristic $T_1$ or $T_2$ distribution for the facies (permeability vs. porosity plot) from a facies-NMR-look-up table.

Figure 17:
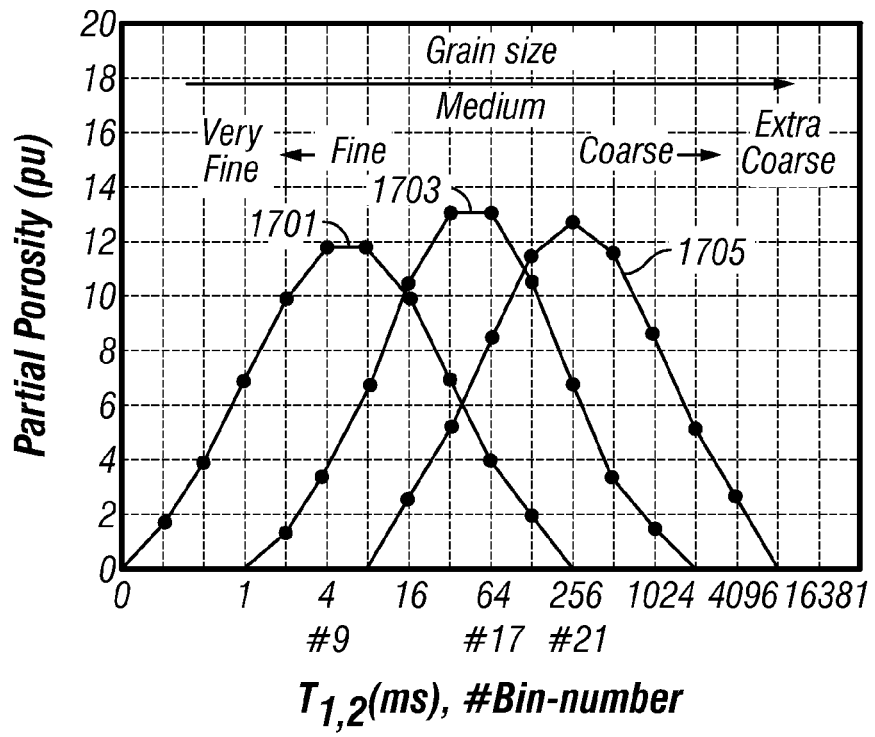
FIG. 17 shows simulation results for 100% water saturation.

For very well sorted grain sizes (not necessarily the case for the data of FIG. 16), the $T_2$ distribution of Petrofacies (with grain size as parameter) can be simulated as shown in the FIG. 17. In this case of simulation using the methods of Georgi is basically uni-modal, where the position of the $T_2$ logarithmic mean value can be correlated with the permeability, following e.g. SDR perm-model. The $T_2$ distribution for three different grain sizes for 100% water saturation is shown by 1701, 1703, 1705. The bin numbers correspond to $T_2$ values ranging logarithmically from 0.25 ms to 16381.37 ms. Real rocks may include a combination of unimodal distributions, giving rise to a multimodal distribution.

Figure 18:
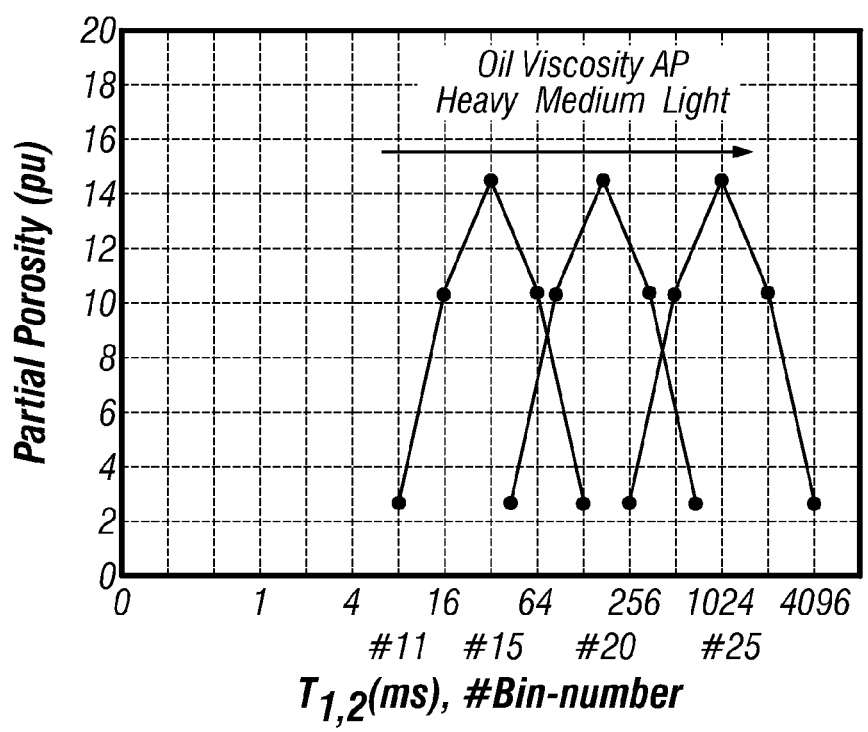
FIG. 18 shows simulation results for 100% oil saturation.
Figure 19:
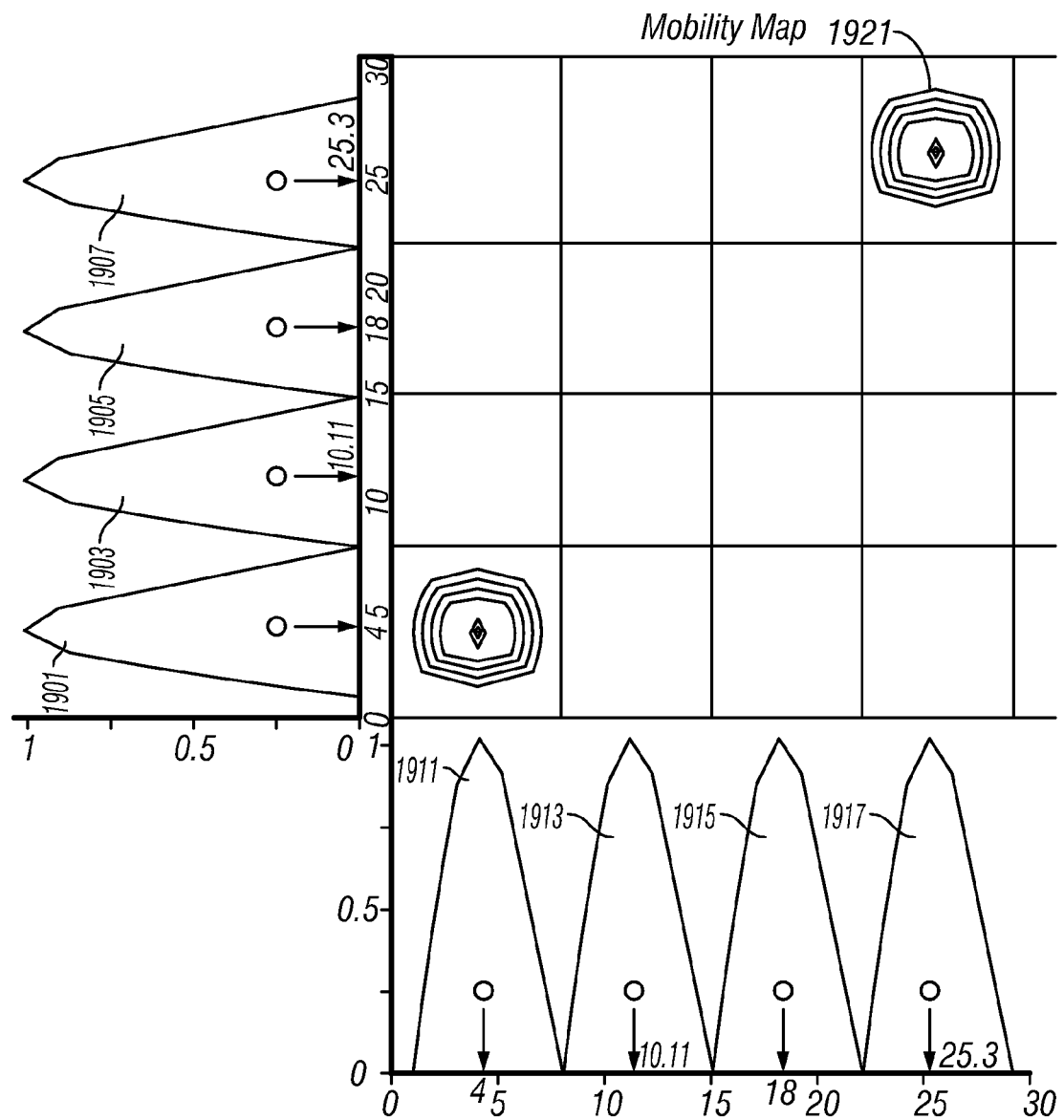
FIG. 19 is a mobility map for a reservoir.

In FIG. 18, the simulation of different oil types in absence of any field gradient (this means is equal to $T_2$ intrinsic—no diffusion effect. When increasing the oil API gravity from around 12 (heavy oil) up to 40 API (light) the FIG. 18 shows that, in general, the lighter the oil and hence the smaller its viscosity, the $T_2$ or $T_1$ distribution shifts to the right on the x-axes (ms or # of Bin). The $T_1$ or $T_2$ distribution of oil can be obtained using Diffusivity-T2 maps (DT2 maps) as discussed above. Gas, which has very low viscosity, would lie at the right end of the scale.

As the location of the distribution along the $T_2$ axes for 100% water saturated sample, not only corresponds to grain size and hence facies, but also to permeability (SDR equation $K_{SDR}=a'\phi^m(T_{2LM})^{M}$ with a: constant; m, n: exponents parameters, $\phi$: porosity and $T_{2LM}$: T2 log mean of the distribution), and the location of the distribution for oil samples along the same $T_2$ axes corresponds to the oil API gravity and much better to viscosity-, it is possible to generate a mobility (permeability over viscosity) map. Up to some geometrical variables, the mobility shows the proportionality between flow rate and differential pressure (Darcy's law):

$$Q=(k/\mu)*\Delta p:$$

Where Q is the flow rate.
  K: permeability.
  $\mu$: viscosity.
  $\Delta p$: differential pressure.

As, in general, the inverse of the oil viscosity is proportional to $T_{2oil}$ the mobility $(k/\mu)$ is therefore proportional to $k*T_{2oil}$. Being k proportional to $T_{2water}$, we obtain the mobility map by multiplying $T_{2water}*T_{2oil}$. The map is shown in the FIG. 19.

The abscissa of this mobility plot is the viscosity indicator derived from $T_1$ or $T_2$ as discussed above. The ordinate is $T_1$ or $T_2$ distribution of water in a porous medium. 1901, 1903, 1905 and 1907 refer to the distributions for microporosity, mesoporosity, macroporosity and megaporosity respectively. C.f. FIG. 16. 1911, 1913, 1915 and 1917 refer to extra-heavy oil, heavy oil, medium oil and light oil respectively.

In general, when for a given reservoir or oil bearing layer, the spot on the map falls on the right up corner the fluid mobility is high 1921 (the best case in terms of production); however, if the spot falls on the lower left corner, 1923 the opposite situation occurs. In situations in which a strict classification of rock quality (facies) and oil viscosity (or API gravity) in terms of $T_1$ or $T_2$ windows, does not hold in every situation, the maps has a universal validity as it represents the Darcy's Law, and can be use to show tendencies in a reservoir evaluation. When spots have a tendency to be above the diagonal with positive slope, it can be understood as that the rock quality overweights the fluid quality.

The method of the present disclosure is described above with reference to a wireline-conveyed NMR logging tool. The method may also be used on logging tools conveyed on coiled tubing in near horizontal boreholes. The method may also be used on NMR sensors conveyed on a drilling tubular, such as a drillstring or coiled tubing for Measurement-While-Drilling (MWD) applications. As is standard practice in well-logging, the results of the processing are recorded on a suitable medium. Implicit in the processing of the data is the use of a computer program implemented on a suitable machine readable medium that enables the processor to perform the control and processing. The machine readable medium may include ROMs, EPROMs, EAROMs, Flash Memories and Optical disks.

While the foregoing disclosure is directed to the specific embodiments of the disclosure, various modifications will be apparent to those skilled in the art. It is intended that all variations within the scope and spirit of the appended claims be embraced by the foregoing disclosure.

What is claimed is:

1. A method of evaluating an earth formation, the method comprising:
  conveying a logging tool into a borehole;
  obtaining nuclear magnetic resonance (NMR) signals at a plurality of depths in the borehole;
  processing the NMR signals to obtain a distribution of a relaxation time at each of the plurality of depths, each of the distributions comprising a plurality of bins;
  producing, from the plurality of relaxation time distributions, a plurality of NMR bin logs of relaxation time values for each of the plurality of bins;
  determining a measure of similarity of a first log indicative of hydrocarbon content in the formation with each of the plurality of NMR bin logs; and
  using the measure of similarity for each of the plurality of NMR bin logs to identify a subset of the plurality of NMR bin logs indicative of hydrocarbon.

2. The method of claim 1 wherein the NMR signals comprise spin-echo signals and the relaxation time comprises a transverse relaxation time $T_2$.

3. The method of claim 1 wherein the measure of similarity is at least one of: (i) a Pearson correlation coefficient, (ii) a p-value characterizing a probability of an observed correlation coefficient, and (iii) mutual information.

4. The method of claim 1 wherein the first log is at least one of: (i) a gamma ray log, and (ii) a resistivity log.

5. The method of claim 1 wherein determining the measure of similarity further comprises performing at least one of: (i) a cross-correlation of the first log with at least one of the plurality of NMR bin logs, and (ii) determination of a mutual information between the first log and at least one of the plurality of NMR bin logs.

6. The method of claim 2 further comprising:
  (i) obtaining additional spin echo signals at each of the plurality of depths while applying an external magnetic field gradient;
  (ii) processing the spin echo signals and the additional spin echo signals to obtain a distribution of a diffusion coefficient (D) at each of the plurality of depths, each of the distribution of diffusion coefficients comprising a plurality of diffusion bins;
  (iii) producing, from the plurality of diffusion coefficient distributions a plurality of diffusion coefficient bin logs of diffusion coefficient bin values corresponding to each of the plurality of diffusion bins;
  (iv) determining a measure of similarity of the first log with each of the plurality of diffusion coefficient bin logs; and
  (v) using the measure of similarity for each of the plurality of diffusion coefficient bin logs to identify a subset of the diffusion coefficient bin logs indicative of hydrocarbon.

7. The method of claim 2 further comprising using the identified subset of the logs and a $T_2$ distribution at at least one of the plurality of depths to obtain a modified $T_2$ distribution responsive primarily to at least one of: (i) water, and (ii) oil in the formation.

8. The method of claim 7 further comprising estimating from the modified distribution at least one of: (i) water saturation, (ii) clay bound water, (iii) bound water irreducible, (iv) moveable water, (v) permeability, and (vi) hydrocarbon content.

9. The method of claim 1 further comprising conveying the logging tool into the borehole on a conveyance device selected from (i) a wireline, and (ii) a drilling tubular.

10. An apparatus for evaluating an earth formation, the apparatus comprising:
a logging tool configured to be conveyed into a borehole, the logging tool further configured to obtain nuclear magnetic resonance (NMR) signals at a plurality of depths in the borehole; and
at least one processor configured to:
(A) process the NMR signals to obtain a distribution of a relaxation time at each of the plurality of depths, each of the distributions comprising a plurality of bins,
(B) use the plurality of relaxation time distributions to produce a plurality of NMR bin logs of relaxation time values for each of the plurality of bins,
(C) determine a measure of similarity of a first log indicative of hydrocarbon content in the formation with each of the plurality of NMR bin logs, and
(D) use the measure of similarity for each of the plurality of NMR bin logs to identify a subset of the NMR bin logs indicative of hydrocarbon.

11. The apparatus of claim 10 wherein the NMR signals comprise spin-echo signals and the relaxation time comprises a transverse relaxation time ($T_2$).

12. The apparatus of claim 10 wherein at least one processor is further configured to use, as the measure of similarity, at least one of: (i) a Pearson correlation coefficient, and (ii) a p-value characterizing a probability of an observed correlation coefficient, and (iii) mutual information.

13. The apparatus of claim 10 further comprising at least one of a gamma ray logging tool and a resistivity logging tool and wherein the first log is at least one of: (i) a gamma ray log, and (ii) a resistivity log.

14. The apparatus of claim 10 wherein the at least one processor is configured to determine the measure of similarity by further performing at least one of: (i) a cross-correlation of the first log with at least one of the plurality of NMR bin logs, and (ii) determination of a mutual information between the first log and at least one of the plurality of NMR bin logs.

15. The apparatus of claim 11 wherein the logging tool is further configured to obtain additional spin echo signals at each of the plurality of depths while applying an external magnetic field gradient; and wherein the processor is further configured to:
(i) process the spin echo signals and the additional spin echo signals to obtain a distribution of a diffusion coefficient at each of the plurality of depths, each of the distribution of diffusion coefficients comprising a plurality of diffusion bins;
(ii) produce, from the plurality of diffusion coefficient distributions, a plurality of diffusion coefficient bin logs of diffusion coefficient bin values for each of the plurality of diffusion bins;
(iii) determine a measure of similarity of the first log with each of the plurality of diffusion coefficient bin logs; and
(iv) use the measure of similarity for each of the plurality of diffusion coefficient bin logs to identify a subset of the diffusion coefficient bin logs indicative of at least one of: (i) hydrocarbon, and (ii) water.

16. The apparatus of claim 11 wherein the processor is further configured to use the identified subset of the logs and a $T_2$ distribution at at least one of the plurality of depths to obtain a modified $T_2$ distribution responsive primarily to water in the formation.

17. The apparatus of claim 16 wherein the processor is further configured to estimate from the modified distribution at least one of: (i) water saturation, (ii) clay bound water, (iii) bound water irreducible, (iv) moveable water, (v) permeability, and (vi) hydrocarbon content.

18. The apparatus of claim 10 further comprising a conveyance device configured to convey the logging tool into the borehole, the conveyance device selected from (i) a wireline, and (ii) a drilling tubular.

19. A computer readable medium product having stored instructions thereon that when read by at least one processor cause the at least one processor to:
process spin echo signals obtained at a plurality of depths in the borehole in the earth formation to estimate a distribution of a transverse relaxation time ($T_2$) at each of the plurality of depths, each of the distributions comprising a plurality of bins,
use the plurality of relaxation time distributions to produce a plurality of NMR bin logs of relaxation time values corresponding to each of the plurality of bins,
determine a measure of similarity of a first log indicative of hydrocarbon content in the formation with each of the plurality of NMR bin logs, and
use the measure of similarity for each of the plurality of NMR bin logs to identify a subset of the NMR bin logs indicative of hydrocarbon.

20. The medium of claim 19 further comprising at least one of: (i) a ROM, (ii) an EPROM, (iii) an EAROM, (iv) a flash memory, and (v) an optical disk.

* * * * *